US010239991B2

(12) United States Patent
Meijboom et al.

(10) Patent No.: US 10,239,991 B2
(45) Date of Patent: Mar. 26, 2019

(54) LIQUID TRIBLOCK COPOLYMER

(71) Applicant: INGELL TECHNOLOGIES HOLDING B.V., Groningen (NL)

(72) Inventors: Ronald Meijboom, Groningen (NL); Theo Flipsen, Groningen (NL); Mike De Leeuw, Groningen (NL)

(73) Assignee: INGELL TECHNOLOGIES HOLDING B.V., Groningen (NL)

( * ) Notice: Subject to any disclaimer, the term of this patent is extended or adjusted under 35 U.S.C. 154(b) by 0 days.

(21) Appl. No.: 15/307,862

(22) PCT Filed: Apr. 29, 2015

(86) PCT No.: PCT/EP2015/059358
§ 371 (c)(1),
(2) Date: Oct. 31, 2016

(87) PCT Pub. No.: WO2015/165976
PCT Pub. Date: Nov. 5, 2015

(65) Prior Publication Data
US 2017/0066874 A1 Mar. 9, 2017

(30) Foreign Application Priority Data

May 1, 2014 (EP) .................................. 14166773

(51) Int. Cl.
*C08G 63/664* (2006.01)
*C08G 64/18* (2006.01)
*A61K 9/00* (2006.01)
*C12N 9/00* (2006.01)
*A61K 31/167* (2006.01)
*A61K 31/635* (2006.01)
*A61K 38/47* (2006.01)
*A61K 47/34* (2017.01)
*A61L 27/18* (2006.01)
*A61L 27/54* (2006.01)
*A61L 27/58* (2006.01)

(52) U.S. Cl.
CPC .......... *C08G 63/664* (2013.01); *A61K 9/0024* (2013.01); *A61K 31/167* (2013.01); *A61K 31/635* (2013.01); *A61K 38/47* (2013.01); *A61K 47/34* (2013.01); *A61L 27/18* (2013.01); *A61L 27/54* (2013.01); *A61L 27/58* (2013.01); *C08G 64/183* (2013.01); *C12N 9/00* (2013.01); *C12Y 302/01017* (2013.01); *A61L 2400/06* (2013.01); *A61L 2430/00* (2013.01)

(58) Field of Classification Search
None
See application file for complete search history.

(56) References Cited

U.S. PATENT DOCUMENTS

| 7,740,877 B2 | 6/2010 | Kim et al. |
| 2003/0082234 A1 | 5/2003 | Seo et al. |
| 2004/0001872 A1 | 1/2004 | Shih et al. |
| 2007/0265356 A1 | 11/2007 | Kim et al. |

FOREIGN PATENT DOCUMENTS

| EP | 2 343 046 A1 | 7/2011 | |
| WO | 99 21908 A1 | 5/1999 | |
| WO | WO 99/21908 * | 5/1999 | ............... A61K 9/06 |
| WO | 2007 019439 A2 | 2/2007 | |
| WO | WO 2007/019439 * | 2/2007 | ............. A61K 47/34 |
| WO | 2011 083086 A1 | 7/2011 | |
| WO | 2012 131104 A2 | 10/2012 | |
| WO | WO 2012/131104 * | 10/2012 | ............. A61K 47/34 |

OTHER PUBLICATIONS

Yu, L., et al., A Subtle End-Group Effect on Macroscopic Physical Gelation of Triblock Copolymer Aqueous Solutions, Angew Chem. Int., Ed. 2006, vol. 45, pp. 2232-2235, Wiley-VCH, XP 2586068A.

* cited by examiner

*Primary Examiner* — Brian Gulledge
(74) *Attorney, Agent, or Firm* — Hudak, Shunk and Farine Co., LPA

(57) ABSTRACT

A bioresorbable triblock copolymer according to Formula 1

R-B-A-B-R    (1)

wherein A is a hydrophilic polymer, B a hydrophobic polymer and R are end-groups, wherein R is H or a C1-C30 organic moiety and wherein the copolymer is fluid in a temperature range of 0° C. to 37° C. A pharmaceutical composition including the triblock copolymer and at least one therapeutically active agent. The copolymer and pharmaceutical composition can be used for forming a depot in a human or animal body or as medical device.

17 Claims, 8 Drawing Sheets

LIQUID TRIBLOCK COPOLYMER

FIELD OF THE INVENTION

The invention relates to bioresorbable triblock copolymers that are liquid at ambient conditions enabling injection into a human or animal body. After injection into said body the liquid copolymers form a (semi-)solid cohesive mass. These liquid copolymers allow encapsulation of therapeutically active agents (API) and after injection into a body slowly release said therapeutically active agents. These liquid polymers can also function as a medical device after injection into a body either or not in combination with biologically active agents.

BACKGROUND OF THE INVENTION

Controlled release of therapeutically active agents, also named biologically active agents, has become essential in treatments of humans and animals. Especially of interest is controlled release of therapeutically active agents locally in a body, such as in tissues or organs for either direct on-site treatment or for systemic uptake.

In recent years, a number of bioresorbable polymers fabricated into product shapes as microspheres, strands, rods and the like have been developed for this reason. The active agent is incorporated into the interior of the polymer product and is after administration to the human or animal body slowly released by different mechanisms. One of the downsides of these products is the laborious process of incorporating the active agents in their interior, that may involve either organic solvents or elevated temperatures. Many active agents will not well survive such circumstances.

An important improvement was found in the use of amphiphilic copolymers, especially triblock copolymers BAB with poly(ethylene glycol) as the central hydrophilic block A flanked by hydrophobic, hydrolysable blocks B. Some of these BAB triblock copolymers have been modified with polymer hydroxyl end-groups comprising fatty acid residues. Said copolymers may form micelles in aqueous solutions and subsequently may form gels at elevated temperatures, such as at 37° C. They may contain at least one therapeutically active agent. For example WO 2011/083086 describes end-capped triblock copolymers that can be used for slow release of therapeutically active agents in human or animal bodies. A disadvantage of these systems is the burst release of therapeutically active agents that may occur after injection of the polymer-drug formulation into a body. Another disadvantage is the limited amount of hydrophobic drugs that can be contained within the hydrogel. Another disadvantage is the limited stability of these hydrolysable triblock copolymers once formulated with water and one or more therapeutically active agents.

US2007/0265356 discloses triblockcopolymers and thermoreversible gels containing said triblockcopolymers with water. The gels also can contain a drug and can be used as slow release system for drugs.

WO2012/131104 discloses triblockcopolymers and thermoreversible gels containing said triblockcopolymers with water. The gels also can contain a drug and can be used as slow release system for drugs. WO99/21908 discloses bioresorbable BAB triblock copolymers having the general structure [polyester]-[polyalkyleneoxide]-[polyester]. The BAB triblock copolymers can be a liquid or a paste. The water insoluble BAB triblock copolymers are blended with water-soluble liquid polymers and a hydrophobic drug.

US2003082234 describes a liquid polymeric composition capable of forming a physiologically active substance containing implant in a living body, said composition comprising a water-soluble biocompatible liquid polyethylene glycol derivative, a biodegradable block copolymer which is insoluble in water but soluble in the said polyethylene glycol derivative, and a physiologically active substance.

US2004001872 describes a composition comprising a BAB block copolymer, a liquid polyethylene glycol and a physiologically active substance.

Disadvantage of the liquid BAB copolymers of the prior art is, that they are used in combination with solvent or liquid polymer additives to make injectable pharmaceutical compositions. In some cases the BAB copolymers have rather high molecular weights and low molecular weight polymers like for example polyethylene glycol are added to make the composition injectable. In other cases the liquid BAB copolymer are used as plasticizers for higher molecular weight block copolymers to make an injectable composition. Addition of these low molecular weight polymers give rise to high burst releases, and an unwanted fast release of the low molecular weight polymer, which may give negative physiological side effects. In yet many other cases water is added to prepare thermoreversible gels, which however show burst release and relative short release times of drugs. None of the known liquid BAB copolymers have been used as such in combination with therapeutically active agents in order to prepare pharmaceutical compositions.

SUMMARY OF THE INVENTION

The object of the present invention is to provide a triblock copolymer which addresses one or more of the above disadvantages, and can be produced in a robust and simple process.

The object is achieved by providing a bioresorbable triblock copolymer according to Formula 1

$$R\text{-}B\text{-}A\text{-}B\text{-}R \qquad (1)$$

wherein A is a hydrophilic polymer, B a hydrophobic polymer and R is an end-group, wherein R is H or C1-C30 organic moiety and wherein the copolymer is fluid in a temperature range between 0 and 37° C.

An advantage of the triblock copolymer according to the invention is that a composition containing the liquid block copolymer and a therapeutically active agent is easy to produce as the therapeutically active agent can be directly mixed with the liquid block copolymer.

A further advantage is that the copolymer according to the invention forms the basis of a new drug delivery system, which can allow the containment of large amounts of drugs. Furthermore the composition containing the block copolymer according to the invention and a therapeutically active agent may be administered at room temperature as a low viscosity liquid, using a small gauge needle, thus minimizing discomfort for a patient. Surprisingly, once injected into the body the compositions form a well-defined, quasi-solid depot that will be localized at the desired site within the body. The depots disintegrate due to solvation of single polymer chains at the outside of them optionally supported by hydrolysis of these chains. The solvated polymer chains or parts thereof are either directly or indirectly excreted by the body in a natural manner. Indirectly here means that solvated polymer chains may further hydrolyze in the body before excretion. The formation of a subcutaneous depot is very surprising, since the composition is a liquid composition.

A further advantage of the block copolymers according to the invention is that the block copolymers once formulated with a therapeutically active agent do not have to contain water as solvent nor any organic solvents, resulting in an improved shelf-life at broader temperature storage conditions by avoiding chemical interaction between solvent, polymer and/or therapeutically active agent.

Another advantage of the block copolymers according to the invention is that the release of a therapeutically active agent is well-controlled and a burst release directly after administration of the copolymer is significantly less or almost absent compared to systems of the prior art.

Another advantage of the block copolymers according to the invention is that therapeutically active agents can be present in the complete depot and, for example, not only in micelles that would be present within a depot containing water as solvent. This is in particular relevant for hydrophobic therapeutically active agents as these are, in the depots according to the prior art, only present in the micelles.

Another advantage of the block copolymers according to the invention is that they form a (semi-)solid once injected into the body of a human or animal that allows the use for tissue filling, tissue separation or other medical purposes. Such use could well be without any therapeutically active agent, but if the therapy requires such, could be a combination with therapeutically or biologically active agents.

RBABR Block Copolymer

A bioresorbable polymer is herewith defined as a polymer that can be metabolized by and/or secreted from the body.

The triblock copolymer according to the invention is fluid at the entire temperature range between 0° C. and 37° C.

Notwithstanding the foregoing the copolymer may also show fluid behaviour outside this temperature range. The term fluid may also be replaced by liquid, but for the invention both refer to a polymer that is in a fluid state without the help of any solvent or plasticizer.

The fluid behaviour of the triblock copolymer according to the invention is measured by its dynamic viscosity under shear. The dynamic viscosity was measured using a TA Instruments AR2000Ex rheometer with a plate-cone setup, type 40 mm cone, angle 1:00:00 deg:min:sec. During the viscosity measurement, the temperature was kept constant at either 20° C. or 37° C., with a shear rate of 5 s$^{-1}$ during 300 s. Average viscosity values were calculated using software (Trios software, TA Instruments). In this way the average dynamic (shear) viscosity of the polymer is determined. The viscosity determined at 37° C. preferably has a value below 30 Pa·s, more preferably below 20 Pa·s or below 10 Pa·s, most preferably below 5 Pa·s, below 3 Pa·s, below 2 Pa·s, or below 1 Pa·s. Typically the viscosity at 37° C. is above 0.1 Pa·s.

The viscosity determined at 20° C. typically has a value above 0.1 Pa·s. The viscosity determined at 20° C. preferably has a value below 30 Pa·s, more preferably below 20 Pa·s or below 10 Pa·s, most preferably below 5 Pa·s.

The viscosity of the triblockcopolymer according to the invention ranges between 0.1 and 30 Pa·s at a temperature of 20° C., preferably between 0.2 and 20 Pa·s, most preferably between 0.3 and 10 Pa·s.

The copolymers of the invention have low to very low glass transition temperatures. The glass transition temperature ($T_g$) is determined by differential scanning calorimetry (DSC) and defined as the midpoint of the thermal transition. The copolymer preferably has a $T_g$ (midpoint) below −20° C., more preferably below −30° C. and most preferably below −40° C.

The copolymers of the invention have low to very low melt temperatures. The melt temperature ($T_m$) is determined by differential scanning calorimetry (DSC) and defined as the midpoint of the thermal transition. The copolymer preferably has a $T_m$ (midpoint) below 20° C., more preferably below 10° C. and most preferably below 0° C.

The number average molecular weight (Mn) of the triblock copolymer preferably is between 500 and 5,000 g/mol, more preferably within the range of 600-3,000 g/mol and most preferably within the range of 700-2,500 g/mol.

The block ratio, in the context of the invention, is the ratio between the sum of the number average molecular weights ($M_n$) of both hydrophobic blocks without counting the end-group modification (the sum of the two B blocks) and the A-block. The required block ratio depends on the hydrophobic block composition (i.e. B-blocks), the degree of modification and the nature of the organic end-group.

In an embodiment of the invention the block ratio, defined as the ratio between the sum of the number average molecular weight of the B-blocks and the number average molecular weight of the A-block, ranges between 0.3 and 20, preferably between 0.5 and 10.

In the present invention, the organic end-groups reduce the viscosity of the triblock copolymers and with that improve their injectability. The organic end-group also has a remarkable effect on controlling the release kinetics of a loaded therapeutically active agent. More in particular, the organic end-group slows down the release of a loaded therapeutically active agent.

A Moiety

The A block in the triblock copolymer is a hydrophilic polymer block. Preferably, the A block is chosen from the group consisting of polyethyleneglycol (PEG), polypropyleneoxide (PPO), polytetramethyleneoxide (PTMO), copolymers of PEO and PPO, polyvinylpyrrolidone (PVP) or poly [N-(2-hydroxyethyl)-L-glutamine] (PHEG). Poly(ethylene glycol) is a diol also known as poly(ethylene oxide) (PEO) and both names can be used interchangeably for the purpose of this invention.

More preferably, the A block is PEG, most preferably the A block is a linear PEG.

The A block preferably has a number average molecular weight (Mn) of at least 100 g/mol, more preferably at least 120 g/mol and most preferably at least 150 g/mol. The weight average molecular weight of the A block preferably is at most 1,500 g/mol, more preferably at most 1,250 g/mol, most preferably at most 1,000 g/mol. For example the molecular weight of the A block is between 180 and 700 g/mol. The molecular weight of the PEG is chosen such that is does not crystallize or only slowly once being part of the triblock copolymers of the current invention. An important aspect is the effect the particular PEG has on the viscosity of the liquid triblock copolymer obtained with it. Another important aspect is the ability of the polymers of the present invention to take up aqueous liquid, after they have been injected in a human or animal body. The amount of aqueous liquid that is being taken up affects the softness of the material and, if one or more therapeutically active agents are incorporated, the release rate of these agents.

B Moiety

The triblock copolymer comprises two B blocks flanking the A block. The B blocks are hydrophobic polymers.

The B blocks in the triblock copolymer may be hydrophobic blocks made by ring-opening polymerization of 2 or more cyclic monomers and with a number average molecular weight range between 400 and 3,000 g/mol. Preferably, the number average molecular weight of each B block ranges between 450 and 2,000 g/mol, more preferably between 500 and 1,500 g/mol.

Both B blocks can be the same or different, preferably both B blocks are the same.

Cyclic monomers used to make B blocks are selected from the group consisting of glycolide, lactide, ε-caprolactone, p-dioxanone (1,4-dioxan-2-one), trimethylene carbonate (1,3-dioxan-2-one), 1,4-dioxepan-2-one (including its dimer 1,5,8,12-tetraoxacyclotetradecane-7,14-dione), 1,5-dioxepan-2-one, 6,6-dimethyl-1,4-dioxan-2-one, 2,5-diketomorpholine, pivalolactone, chi.-diethypropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one, β-propiolactone, γ-butyrolactone, δ-valerolactone, ε-decalactone, 3-methyl-1,4-dioxane-2,5-dione, 1,4-dioxane-2,5-dione, 2,5-diketomorpholine, α,α-diethylpropiolactone, γ-butyrolactone, 1,4-dioxepan-2-one, 1,5-dioxepan-2-one, 6,6-dimethyl-dioxepan-2-one, 6,8-dioxabicycloctane-7-one, 5,5-dimethyl-1,3-dioxan-2-one, or preferably of the group consisting of glycolide, lactide, ε-caprolactone, δ-valerolactone, 1,3-dioxan-2-one (also known as trimethylene carbonate), 5,5-dimethyl-1,3-dioxan-2-one, 1,4-dioxan-2-one, 1,4-dioxepan-2-one and 1,5-dioxepan-2-one.

Cyclic monomers used to make B blocks are most preferably selected from the group consisting of glycolide, lactide, ε-caprolactone, δ-valerolactone, 1,3-dioxan-2-one (also known as trimethylene carbonate) and 1,4-dioxan-2-one (also known as p-dioxanone).

Hydrophobic blocks, containing the monomeric units described above, mainly contain ester and/or carbonate bonds, making them hydrolysable. They can be prepared in a range of well-defined molecular weights.

The choice of monomers is based on the effect they have on the viscosity of the triblock copolymers obtained with them. Another important aspect is the effect they have on the rate and profile of bioresorption that one wants to achieve with the triblock copolymer in vivo. Polyesters made by combining aforementioned monomers have been studied for a while and some of the combinations are well-known.

In most cases, the combinations involve only 2 monomers, although examples with 3 different monomers in a B block are possible and can be beneficial.

In a preferred embodiment each B block is a combination of ε-caprolactone with anyone of lactide, glycolide, δ-valerolactone, p-dioxanone or trimethylenecarbonate; or a combination of δ-valerolactone with anyone of lactide, glycolide, p-dioxanone or trimethylenecarbonate; or a combination of p-dioxanone with lactide, glycolide or trimethylenecarbonate; or a combination of trimethylenecarbonate with lactide or glycolide.

R End-Groups

The bioresorbable triblock copolymer according to the invention comprises two R end-groups. B-A-B triblocks are modified by using the terminal hydroxyl group of the B blocks. Preferably, R is H or a C1-C30 organic moiety, more preferably R is a C1-C30 organic moiety. The organic moiety can be linear, cyclic or branched. The organic moiety may contain heteroatoms, like for example O, N and I. Examples of an organic moiety are fatty acid residues, ether residue or urethane residue. The fatty acid residue is obtained by the reaction of a fatty acid or activated fatty acid with the hydroxyl group of the end of a B-block. Fatty acids include a selection of saturated or unsaturated fatty acids of 1 to 30 carbon atoms, preferably 2 to 20 carbon atoms. The fatty acids groups can contain heteroatoms, like for example iodine. The presence of iodine can assist in visualizing the depot during and after injection into an animal or human body.

The C1-C30 fatty acid can be selected from the group consisting of acetic acid, propionic acid, butyric acid, pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, nonadecanoic acid, eicosanoic acid, heneicosanoic acid, docosanoic acid, tricosanoic acid, tetracosanoic acid, pentacosanoic acid, hexacosanoic acid, heptacosanoic acid, octacosanoic acid, nonacosanoic acid, triacontanoic acid, caproic acid, caprylic acid, capric acid, lauric acid, myristic acid, myristoleic acid, palmitic acid, palmitoleic acid, stearic acid, oleic acid, linoleic acid, alpha-linoleic acid, gamma-linoleic acid, stearidonic acid, rumenic acid, beta-calendic acid, eleostearic acid, puninic acid, parinaric acid, pinolenic acid, arachidic acid, eicosenoic acid, eicosadienoic acid, eicosatrienoic acid, dihomo-gamma-linolenic acid, mead acid, eicosatetraenoic acid, arachidonic acid, or eicosapentaenoic acid.

Preferably, R is chosen from an acetyl group, a propionyl group, a butyryl group, a pentanoyl group, a hexanoyl group, a nonanoyl group, a dodecanoyl group, a pentadecanoyl group, a 2-n-hexyldecanoyl group, a stearoyl group or a benzoyl group, wherein each R can be optionally substituted with heteroatoms like for example iodine. R can be linear, branched or cyclic and saturated or unsaturated.

Naturally occurring fatty acids are easily degradable through the acetyl-coenzyme A cycle. Furthermore these acids have less risk of exhibiting toxicity in vivo in quantities used in the scope in the present invention. Some of them could have beneficial or detrimental biological activities though. A person skilled in the art would have to take the fatty acid choice into account, depending on the application and the location in the body. Modification with longer fatty acid derivatives will generally increase the resorption time of the polymer.

Coupling fatty acids to the B-A-B triblock copolymers may involve the use of coupling agents like, but not limited to, isocyanates or the derivatisation of either the fatty acids or the polymer end-groups. Functional groups of the fatty acids or polymers can be activated to promote coupling by using activating agents like, but not limited to, carbonyl diimidazole, N-hydroxysuccinimide, para-nitrophenyl chloroformate, succinic anhydride. Direct derivatives of fatty acids like, but not limited to, acid chlorides, anhydrides, isocyanates can also be used, especially since some of them are readily commercially available.

These coupling methods are well-known to the one skilled in the art.

For some applications special moieties may have to be introduced into the fatty acid derivatives used for end group modification. For example, the use of an unsaturated fatty acid may allow chemical reactions to occur between the unsaturated fatty acid chains to achieve polymer crosslinking. Crosslinking is usually carried out in order to modify the mechanical properties and degradation profile of polymers. The activation and intermolecular reaction between those crosslinkable moieties is usually caused by a radiation source, an external chemical reaction or stimulus, or a combination thereof. Radiation examples include, but are not limited to, heat, infrared sources, ultra-violet sources, electron-beam sources, micro-waves sources, x-ray sources, visible light sources [monochromatic or not] and gamma-rays. External reaction, or stimulus include, but are not limited, to pH, oxidation/reduction reactions, reactions with a chemical agent present in vivo (gas, protein, enzymes, antibody etc), reaction with a chemical added to the composition upon introduction into the body, known as dual systems, for example a molecule containing two or more reactive groups.

End-groups may also be chosen from the group of heteroatom alkyls, containing for instance Oxygen, Nitrogen or Iodine atoms.

The choice of the end-group is based on the effect they have on the viscosity of the triblock copolymers obtained with them. Another important aspect is the effect they have on the formation of a (semi-)solid in vivo and on the softness thereof. Another important aspect is the effect they have on the release kinetics of a therapeutically active agent, if such an agent is incorporated in the (semi-)solid formed.

Preferred Copolymers

In one embodiment the bioresorbable triblock copolymer according to formula I is a copolymer wherein A is a linear poly(ethylene glycol) moiety having a molecular weight between 100-1,500 g/mol, more preferably between 120-1,250 g/mol and most preferably between the 150-1,000 g/mol, and wherein B stands for a polyester moiety comprising at least two types of monomers B1 and B2 chosen from the group ε-caprolactone, δ-valerolactone, glycolide, lactide, p-dioxanone (1,4-dioxan-2-one) and trimethylene carbonate (1,3-propylene carbonate), more preferably form the group ε-caprolactone, δ-valerolactone, glycolide, lactide, wherein R is H or a C1-C30 fatty acid residue optionally containing heteroatoms and wherein the molecular weight of the block copolymer is between 500-5,000 Dalton, preferred 600 and 3,000 g/mol, more preferably within the range of 700-2,500 g/mol; and wherein the shear viscosity determined at 20° C. has a value below 30 Pa·s, more preferably below 20 Pa·s or below 10 Pa·s, most preferably below 5 Pa·s; and wherein the copolymer has a $T_g$ (midpoint) below −20° C., more preferably below −30° C. and most preferably below −40° C.

In another embodiment the bioresorbable triblock copolymer according to formula I is a copolymer wherein the block ratio of the triblock copolymer, which ratio is defined as the ratio between the sum of the number average molecular weight of the B-blocks and the number average molecular weight of the A-block, ranges from 0.5 to 10, wherein the A-block is a linear poly-(ethylene glycol) block having a number average weight (Mn) of at least 100 Da and wherein R is chosen from an acetyl group, a propionyl group, a hexanoyl group, a nonanoyl group, a dodecanoyl group, pentadecanoyl group, a stearoyl group or a benzoyl group and wherein each R can be optionally substituted.

In a further embodiment the bioresorbable triblock copolymer according to formula I is a copolymer wherein A is a polyethyleneglycol having a molecular weight between 150 and 700 Da, wherein each B block is a combination of ε-caprolactone with anyone of lactide, glycolide, δ-valerolactone, p-dioxanone or trimethylenecarbonate; or a combination of δ-valerolactone with anyone of lactide, glycolide, p-dioxanone or trimethylenecarbonate; or a combination of p-dioxanone with lactide, glycolide or trimethylenecarbonate; or a combination of trimethylenecarbonate with lactide or glycolide; wherein the R is chosen from an acetyl group, a propionyl group, a hexanoyl group, a nonanoyl group, a dodecanoyl group, pentadecanoyl group, a stearoyl group or a benzoyl group and wherein each R can be optionally substituted, and wherein the molecular weight of the entire block copolymer is between 750 and 3,000 g/mol, more preferably within the range of 1,000-2,500 G/mol; and wherein the shear viscosity determined at 20° C. has a value below 30 Pa·s, preferably below 20 Pa·s, more preferably below 10 Pa·s, most preferably below 5 Pa·s; and wherein the copolymer has a $T_g$ (midpoint) below −20° C., more preferably below −30° C. and most preferably below −40° C.

Pharmaceutical Composition.

The invention is also directed to a pharmaceutical composition comprising the triblock copolymer according to the invention, and at least one therapeutically active agent.

Preferably the pharmaceutical composition contains at least 50 wt % of one or more of the triblock copolymers according to the invention and at least one therapeutically active agent. More preferably the pharmaceutical composition contains at least 70 wt % of one or more of the triblock copolymers according to the invention and at least one therapeutically active agent.

In an embodiment the pharmaceutical composition consists essentially of one or more of the triblock copolymer according to the invention and at least one therapeutically active agent.

Preferably the pharmaceutical composition according to the invention contains less than 1 wt % water.

Preferably, the shear viscosity of the pharmaceutical composition, ranges between 0.01 and 30 Pa·s, more preferably between 0.1 and 20 Pa·s at 20° C.

The invention also relates to a pharmaceutical composition consisting essentially of a triblock copolymer according to Formula 1

R-B-A-B-R         (I)

wherein A is a hydrophilic polymer, B a hydrophobic polymer and each R is an end-group, wherein R is selected from H or a C1-C30 organic moiety and wherein the copolymer is fluid in a temperature range of 0° C. to 37° C.; and at least one therapeutically active agent.

Preferably the pharmaceutical composition comprises a bioresorbable triblock copolymer according to formula I, wherein A is a linear polyethylene glycol) moiety having a molecular weight between 100-1,500 g/mol, more preferably between 120-1,250 g/mol and most preferably between the 150-1,000 g/mol or between 150 and 850 g/mol, and wherein B stands for a polyester moiety comprising at least two types of monomers B1 and B2 chosen from the group ε-caprolactone, δ-valerolactone, glycolide, lactide, p-dioxanone (1,4-dioxan-2-one) and trimethylene carbonate (1,3-propylene carbonate), more preferably form the group ε-caprolactone, δ-valerolactone, glycolide, lactide, wherein R is H or a C1-C30 fatty acid residue optionally containing heteroatoms and wherein the molecular weight of the block copolymer is between 500-5,000 g/mol, preferred 600 and 3,000 g/mol, more preferably within the range of 700-2,500 g/mol; and wherein the shear viscosity determined at 20° C. has a value below 30 Pa·s, more preferably below 20 Pa·s or below 10 Pa·s, most preferably below 5 Pa·s; and wherein the copolymer has a $T_g$ (midpoint) below −20° C., more preferably below −30° C. and most preferably below −40° C.; and at least one therapeutically active agent.

It has been surprisingly found that the viscosity of the pharmaceutical composition is largely determined by the polymer used while the therapeutically active agent has only a minor effect on the injectability of the formulation composition. This is even independent from the molecular weight of the therapeutically active agent and the hydrophobicity of the therapeutically active agent. Moreover, an advantage of the pharmaceutical composition of the present invention, is that even hydrophilic therapeutically active agents, like for example Lidocaine and Lidocaine.HCl,) demonstrate a slow to very slow release.

Therapeutically Active Agent

By therapeutically active agents people skilled in the art refer to any set of molecules, cells or cell materials able to prevent, slow down, moderate or cure a disease in, or that can deliver a desired therapeutic effect on, a treated human or animal. Human diseases are also referred to as defined by the World Health Organization in the WHO ICD-10 (2007) classification document.

The active ingredient in the composition of the present invention may be an active ingredient such as any therapeutically active ingredient and any diagnostic and any contrast agent and includes those therapeutically active ingredients having a prophylactic effect on the animal, including human as well as those therapeutically active ingredients that have an effect of alleviating, reducing or even completely eliminating a symptom, or a cause, or a consequence of a disease, such as pain, swelling or inflammation or a disease from the animal, including human. For example, the therapeutically active ingredient may include broad classes of compounds normally delivered into the body. For example, these therapeutically active ingredients include but are not limited to anti-infectives (including antibiotics, antivirals, fungicides, scabicides or pediculicides); antiseptics (e.g. benzalkonium chloride, benzethonium chloride, chorhexidine gluconate, mafenide acetate, methylbenzethonium chloride, nitrofurazone, nitromersol and the like); analgesics and analgesic combinations; anorexics; antihelminthics, antiarthritics, antiasthmatic agents; anticonvulsants; antidepressants; antidiabetic agents; antidiarrheals; antihistamines; anti-inflammatory agents, antimigraine preparations; antinauseants; antineoplastics; antiparkinsonism drugs; antipuritics; antipsychotics; antipyretics, antispasmodics; anticholinergics; sympathomimetics; xanthine derivatives; cardiovascular preparations including potassium and calcium channel blockers; beta-blockers; alpha-blockers and antiarrhythmics; antihypertensives; diuretics and antidiuretics; vasodilators including general coronary, peripheral and cerebral vasodilators; central nervous system stimulants; vasoconstrictors; cough and cold preparations, including decongestants; hormones and steroids (e.g. estrogens, progestins, androgens, adrenocorticoids, corticosteroids and the like); hypnotics; immunosuppressives; muscle relaxants; parasympatholytics; psychostimulants; sedatives and tranquilizers, narcotics (e.g. morphine, meperidine, codeine and the like), local anesthetics (e.g. amide- or anilide-type local anesthetics such as bupivacaine, dibucaine, mepivacaine, procaine, lidocaine, tetracaine and the like); antiemetic agents (e.g. ondansetron, granisetron, tropisetron, metoclopramide, domperidone, scopolamide and the like); antiangiogenic agents (e.g. combrestatine, contortrostatin, anti-VEGF and the like), polysaccharides, immune-modulating, anti-thrombogenic compounds, anti-claudicating drugs, anti-atherosclerotic drugs, antihistamines, anti-cancer drugs (e.g. mechlorethamine, cyclophosphamide, fluorouracil, thioguanine, carmustine, lomustine, melphalan, chloambucil, streptozocin, methotrexate, vincristine, bleomycin, vinblastine, vindesine, dactinomycine, daunorubicin, doxorubicin, tamoxifen, paclitaxel, epirubicin, mitomicin C, cisplatin, carboplatin, and the like and photosensitizers used in photodynamic therapy, vascular drugs, ophthalmic drugs, amino acids, vitamins, neurotransmitters, neurohormones, signaling molecules, psychoactive medicaments, synthetic drugs, semi-synthetic drugs, natural drugs and substances derived from these, or combinations of the above.

The therapeutically active ingredient may also be a biological including but not limited to (recombinant) proteins, PEGylated-proteins and peptides (e.g. insulin, erythropoietin, exenatide, glucagon-like-peptide-1, morphogenic proteins (e.g. bone morphogenic proteins, transforming growth factors, fibroblast growth factors, tumor necrosis factors), receptor antagonists (e.g. Interleukin-1-receptor-antagonist), anticancer proteins (e.g. neocarzinostatin, L-asparaginase, interleukin-2, bevacizumab and other anti-VEGF agents) prophylactic vaccines, therapeutic vaccines, genetic materials (e.g. nucleic acid sequences, polynucleotides, (antisense) oligonucleotides, plasmids, DNA, RNA, siRNA, microRNA), aptamers, enzymes, antigens, antibodies, antibody fragments, viruses, virus-based materials, cells, cellular substructures, etc.), Prodrugs, metabolites, derivatives, in-vivo or in in-vitro chemically modified products, in-vivo or in-vitro enzymatic modified products and therapeutically active degradation products of the therapeutically active ingredients described herein are included in the scope of the invention.

Preferably, the active ingredient is a therapeutically active ingredient chosen from the group of immune-modifying drugs, anti-inflammatory drugs or growth factors.

Preferably, the active ingredient is a therapeutically active ingredient chosen from the group of immune-modifying drugs for example cyclosporine, tacrolimus (FK-506), sirolimus or rapamycin.

Preferably, the active ingredient is a therapeutically active ingredient chosen from the group of steroidal anti-inflammatory drugs, for example prednisone, prednisolon, triamcinolon, clobetasol or betamethason.

Preferably, the active ingredient is a therapeutically active ingredient chosen from the group of non-steroidal anti-inflammatory drugs, for example aspirin, diclofenac, piroxicam, meloxicam, ibuprofen or a selective COX-2 inhibitor for example celecoxib, valdecoxib, etoricoxib or rofecoxib.

Preferably, the active ingredient is a therapeutically active ingredient chosen from the group of anticancer agents for example bevacizumab, tamoxifen or interleukin-2.

Preferably, the active ingredient is a therapeutically active ingredient chosen from the group of anti-viral agents for example acyclovir or oseltamivir.

Preferably, the active ingredient is a therapeutically active ingredient chosen from the group of anti-bacterial agents for example amoxicillin.

Preferably, the active ingredient is a therapeutically active ingredient chosen from the group of anti-diabetic agents for example insulin, glucagon-like-peptide-1, exenatide.

Preferably, the active ingredient is a therapeutically active ingredient chosen from the group of vaccines.

Preferably, the active ingredient is a therapeutically active ingredient chosen from the group of ophthalmic agents for example Triamcinolone and Bevacizumab.

Preferably, the active ingredient is a therapeutically active ingredient effective against forms of neuro-degenerative diseases such as apomorphine, rivastigmine, pramipexole, pioglitazone, memantine and safinamide Preferably, the active ingredient is a therapeutically active ingredient chosen from the group of biologicals including but not limited to growth factors which are very suitable for application in orthopedics and in particular in the prevention or treatment of diseases of intervertebral discs, or cartilage, or bone. Examples of such growth factors include but are not limited to transforming growth factor 3, fibroblast growth factor 18, osteogenic protein 1, bone morphogenic protein 2, bone morphogenic protein 6, bone morphogenic protein 7, interleukin-1-receptor-antagonist.

Preferably, the active ingredient belongs to the class of human growth hormones and its biosimilar derivatives, which can be applied in both pediatric and adult growth disorders, maintenance of sufficient musculature, and for anti-ageing applications.

Preferably, the active ingredient is a therapeutically active ingredient effective against inflammation or microbial infections of the inner ear and its connecting tissues, (intratympanic ear diseases).

Preferably, the active ingredient is a therapeutically active ingredient effective against forms of diabetes, for example insulin and glucagon-like-peptide-1, and their derivatives such as exendin-4 and liraglutide.

For the active ingredient which are water soluble, the drug preferably has a solubility in water of at least 20, for example of at least 100, for example of at least 500 µg/ml, for example of at least 1000 µg/ml, for example of at least 5000 µg/ml in water measured at 20° C. and at atmospheric pressure (1 bar).

Examples of water soluble active ingredients include small molecules (of up to 5,000 Da), medium sized molecules (of up to 10,000 Da), but also large molecules (of at least 10,000 Da), such as proteins. These water soluble active ingredients may be synthesized chemically, but may also be a biological including but not limited to (recombinant) proteins and peptides (e.g. insulin, erythropoietin, exenatide, glucagon-like-peptide-1, morphogenic proteins (e.g. bone morphogenic proteins, transforming growth factors, fibroblast growth factors, tumor necrosis factors), receptor antagonists (e.g. Interleukin-1-receptor-antagonist), anticancer proteins (e.g. neocarzinostatin, L-asparaginase, interleukin-2, bevacizumab and other anti-VEGF agents) prophylactic vaccines, therapeutic vaccines, genetic materials (e.g. nucleic acid sequences, polynucleotides, (antisense) oligonucleotides, plasmids, DNA, RNA, siRNA, microRNA), aptamers, enzymes, antigens, antibodies, antibody fragments, viruses, virus-based materials, cells, cellular substructures, etc.).

Therefore, the invention also relates to a composition according to the invention, wherein the active ingredient is a therapeutically active ingredient selected from the group of water soluble drugs, that is drugs that have a solubility in water of at least 20 µg/ml as determined using the method described herein.

The invention also relates to a composition, wherein the composition further comprises nano-particles and/or microparticles (such as liposomes and microspheres) which particles contain any of the therapeutically active ingredients as described above.

Therapeutically active agents include but are not limited to nutrients, pharmaceuticals (small molecular entities), proteins and peptides, vaccines, genetic materials, (such as polynucleotides, oligonucleotides, plasmids, DNA and RNA), diagnostic agents, imaging agents, enzymes, nucleic acid sequences, antigens, antibodies, antibody fragments, viruses, virus-based materials, cells, cell substructures, growth factors, antibiotics, anti-inflammatory compounds, immune-modulating, anti-thrombogenic compounds, anti-claudicating drugs, anti-arrhythmic drugs, anti-atherosclerotic drugs, antihistamines, cancer drugs, vascular drugs, ophthalmic drugs, amino acids, vitamins, hormones, neurotransmitters, neurohormones, enzymes, signaling molecules, psychoactive medicaments, synthetic drugs, semi-synthetic drugs, natural drugs and substances derived from these, or combinations of the above.

An therapeutically active agent or also called active pharmaceutical ingredient (API), may demonstrate any kind of activity, depending on the intended use. The active agent may be capable of stimulating, blocking or suppressing a biological response.

The therapeutic active agents can be used for sustained delivery in many different diseases and conditions within humans and animal.

Furthermore, the depot forming polymers will be completely broken down after having completed their function. This is especially important in the application in the area of intervertebral discs, where there is less metabolic activity.

In still another embodiment the therapeutic active agent is an agent to avoid, control, suppress, or eradicate infectious diseases.

When a therapeutically active agent is present in the polymer composition it can be present in an amount of 0.000001 to 70% by weight relative to the total weight of the composition. Preferably the therapeutically active agent is present in an amount of 0.02 to 50% by weight, more preferably in an amount of 0.05 to 40% by weight.

Even more preferably in the range between 0.1% and 20 wt %, or between 0.5% and 10 wt %.

The invention is also directed to the use of the block copolymer according to the invention or the pharmaceutical composition according to the invention for forming soft matter in an animal or human body after injection.

The invention is also directed to the use of the block copolymer according to the invention or the pharmaceutical composition according to the invention for forming a depot in an animal or human body after injection.

The invention is also directed to the use of the block copolymer according to the invention or the pharmaceutical composition according to the invention as medical device.

The invention also relates to a process for preparing a pharmaceutical composition, comprising the steps of providing a triblock copolymer according to Formula 1

$$R\text{-}B\text{-}A\text{-}B\text{-}R \qquad (1)$$

wherein A is a hydrophilic polymer, B a hydrophobic polymer and each R is an end-group, wherein R is selected from H or a C1-C30 organic moiety and wherein the copolymer is fluid in a temperature range of 0° C. to 37° C.; providing at least one therapeutically active agent and mixing the copolymer with the therapeutically active agent.

Tissue Engineering

Applications of tissue engineering devices comprising copolymers according to the present invention include, but are not limited to, nerve growth or repair, cartilage growth or repair, bone growth or repair, muscle growth or repair, skin growth or repair, secreting gland repair, ophthalmic repair. It should be underlined that the soft matter may be used as such or as a part of a bigger implant, scaffold or structure.

The block copolymers or formulations made with them may also be used as temporary void fillers in case of significant trauma, to prevent adhesion of damage tissues and scar tissue formation while either or not waiting for corrective and reconstructive surgery. Void filling could be performed easily by injecting the polymers of the current invention. Other benefits of using said polymers as void fillers may include but are not limited to: preventing contamination from outside, preventing infection, preventing surrounding tissue necrosis or alteration, inducing specific tissue formation (bone, cartilage, muscle, nerve, skin etc.), helping to maintain structural integrity of the surrounding tissues by itself or by combination with other known scaffolds or structures, trapping specific natural or foreign molecules.

The block copolymers of the current invention may also be used as bioresorbable dermal fillers.

Although the invention has been described in detail for purposes of illustration, it is understood that such detail is solely for that purpose and variations can be made therein by those skilled in the art without departing from the spirit and scope of the invention as defined in the claims.

It is further noted that the invention relates to all possible combinations of features described herein, preferred in particular are those combinations of features that are present in the claims.

It is further noted that the term 'comprising' does not exclude the presence of other elements. However, it is also to be understood that a description on a product comprising certain components also discloses a product consisting of these components. Similarly, it is also to be understood that a description on a process comprising certain steps also discloses a process consisting of these steps.

The invention will hereafter be elucidated by way of the following examples, without being limited thereto.

Examples

DETAILED DESCRIPTION OF THE INVENTION

Materials:

Toluene and n-pentane were purchased from Boom (Meppel, The Netherlands). ε-Caprolactone, triethylamine and propionic anhydride were purchased from Across Organics (New Jersey, USA) and PEG200, PEG600, PEG1000, hexanoic anhydride and tin(II)2-ethylhexanoate from Sigma Aldrich (St. Louis, USA). Lauric anhydride was purchased from ABCR (Karlsruhe, Germany). The API's lidocaine, lidocaine-HCl and lysozyme were purchased from Sigma Aldrich (St. Louis, USA), Celecoxib was purchased from LC Laboratories (Woburn, USA). The monomers L-lactide, D-lactide and glycolide were purchased from Purac (Gorinchem, The Netherlands).

Test Methods

Molecular weights were determined by GPC using an Agilent system Series 100 equipped with a guard column (PLgel 55 μm, 7.5×50 mm) and three Varian columns (PLgel, 5 μm, 500 Å, 300×7.5 mm). Detection was performed with a refractive index detector. PEG standards of different molecular weights were used for reference. The eluent was THF, the elution rate was 1.0 ml/min. The column temperature was 35° C. The concentration of the samples was approx. 4 mg/ml in THF and the injection volume was 50 μl. $M_n$ polymer is the number average molecular weight of the polymer relative to the PEG standards and measured in THF.

Thermal properties of the polymers were determined by DSC (TA Instruments DSC Q2000 apparatus). Samples of approximately 10 mg in closed Aluminium pans were cooled from room temperature to −90° C. and kept isothermal for 5 minutes, after which they were heated to 70° C. with a heating rate of 10° C./min (modulated +/−1° C. every 60 seconds). Next, the samples were cooled to −90° C. with a cooling rate of 5° C./min (modulated +/−1° C. every 60 seconds), followed by a second heating cycle to 70° C. with a heating rate of 2° C./min (modulated +/−1° C. every 60 seconds). Using the second heating run, the glass transition temperature ($T_g$) was determined as the midpoint of heat capacity change and the melting temperature $T_m$ as the maximum temperature of the endothermic area.

Figure 1:
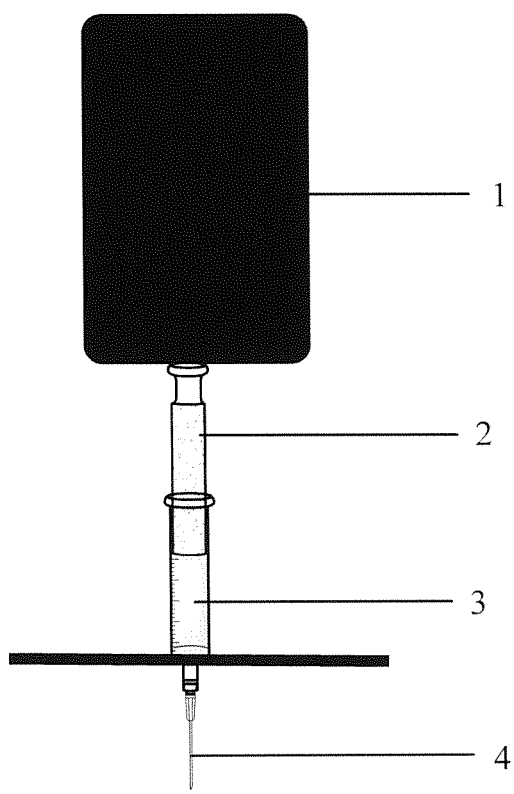
FIG. 1 shows the injectability setup for measuring the ejection time of a block copolymer by means of a syringe.

The injectability of each polymer was determined, by measuring how much time (seconds) was needed to eject a known volume through a needle (metal). In order to measure each sample using the same conditions a set-up was prepared as shown in FIG. 1.

The polymer was charged in a plastic syringe 3 (1 ml) with a luer lock and fitted with a needle 4. Standard metal needles were used: 21 G 0.80×50 mm, 25 G 0.50×25 mm or 27 G 0.40×20 mm. The syringe was locked in a clamp (not shown) and a weight 1 of 3,250 g was placed on the plunger 2. The plunger/weight interface was 0.8 cm$^2$ creating a pressure of 4.06 kg/cm$^2$ For the 21 G, 25 G and 27 G needle the time was measured how long it takes to eject 0.1 ml. Before ejection the syringes with polymer were stored for 2 days at 20° C. The measurements were performed at 20° C. The weight put on the plunger was chosen such that the measurement mimics manual injection.

Viscosity measurements were carried out on a TA Instruments AR2000Ex with a plate-cone setup, type 40 mm cone, angle 1:00:00 deg:min:sec. During the viscosity measurement, the temperature was kept constant at either 20° C. or 37° C., with a shear rate 5 s$^{-1}$ during 300 s. Average viscosity values were calculated using software (Trios software, TA Instruments). In this way the average dynamic (shear) viscosity of the polymer is determined. Results are listed in Table 2 A and B.

General Synthesis Procedure:

In a three-neck round-bottom flask (500 ml) equipped with a Dean Stark trap and a condenser, PEG200 (20.6 g; 103 mmol), L-lactide (51.7 g; 359 mmol), ε-caprolactone (51.5 g; 452 mmol) and 250 ml toluene were introduced and, while stirring, heated to reflux under nitrogen atmosphere. The solution was azeotropically dried by distilling off 110 ml toluene/water. Next, it was cooled down to 90° C. and tin octoate (0.74 g; 1.8 mmol) was added. Ring-opening polymerization was carried out by refluxing the mixture overnight under nitrogen atmosphere. Subsequently, the solution was cooled down to room temperature.

Synthesis 2-n-Hexyldecanoyl Chloride

At ambient temperature, thionylchloride (60 ml, 826 mmol) was added drop wise to a solution of 2-n-hexyldecanoic acid (50 g, 195 mmol) in DCM (200 ml). The obtained mixture was stirred overnight at ambient temperature.

Volatiles were evaporated under reduced pressure at 60° C. Finally the remaining material was stripped (3×) with toluene (100 ml) at 60° C.

Modification Procedures:

Modification with Propionyl End-Group; PEG200(cap$_{50}$-lac$_{50}$)$_{5.0}$-C3

To the reaction mixture, Et$_3$N (52.5 g; 515 mmol; 5 eq.) and propionic anhydride (40 g, 310 mmol, 3 eq.) were added. The resulting mixture was refluxed, while stirring, for 1 hour.

Modification with hexanoyl end-group; PEG200(cap$_{50}$-lac$_{50}$)$_{5.0}$-C6

As described as with the modification with propionic anhydride. Propionic anhydride was replaced by hexanoic anhydride (66.3 g, 310 mmol. 3 eq.).

Modification with dodecanoyl end-group; PEG200(cap$_{50}$-lac$_{50}$)$_{5.0}$-C12

As described as with the modification with propionic anhydride. Propionic anhydride was replaced by lauric anhydride (125 g, 310 mmol. 3 eq.).

Modification with 2-n-hexyldecanoyl end-group; PEG200(cap$_{50}$-lac$_{50}$)$_{5.0}$-2-n-HD Volatiles of the polymer solution were evaporated under reduced pressure at 60° C. The remaining crude polymer was dissolved in DCM (300 ml), followed by the addition of Et$_3$N (52.5 g; 515 mmol; 5 eq.) and 2-n-hexyldecanoyl chloride (30.6 g, 257 mmol, 2.5 eq.) The resulting mixture was stirred for 2 hours at ambient temperature, after which the DCM was evaporated under reduced pressure at 60° C. EtOAc (100 ml) was added and the mixture was stirred for 10 minutes at ambient temperature. The formed solids were filtered off and the filtrate was diluted with DCM (200 ml). The obtained solution was poured into n-pentane (600 ml) containing separation funnel. After shaking, the polymer was allowed to settle to the bottom of the separation funnel. Polymer was collected and dried under reduced pressure at 60° C. and finally dried under high vacuum (<1 mBar) at 60° C. for at least 24 hrs.

General Work-Up Procedure:

The reaction mixture was poured into a separation funnel containing n-pentane (600 ml). After shaking the mixture, the polymer settled to the bottom of the funnel and could be collected. The obtained polymer was dried under reduced pressure for 2 hours at 60° C., followed by further drying in the vacuum oven (<0.2 mBar) at 90° C. for at least 24 hours.

Using this method as described above a library of polymers was prepared. Variations were made by using different PEG blocks, changing type of monomers used in the B-block and length of B block, and varying the endgroups. Results are listed in table 1.

Nomenclature.

In the experimental section abbreviations of triblock copolymers have been used.

For example PEG200(cap$_{50}$-lac$_{50}$)$_{5.0}$ means a triblock copolymer having an A-block made of PEG, having a molecular weight of 200 Da, and on each side of the A-block a B-block, wherein the total weight of the two B-blocks is equal to 5 times the weight of the A-block, and wherein each B-block comprises ε-caprolacton and lactide in a 50/50 (weight) ratio. In this case the RBABR triblock copolymer comprises on average an A block consisting of PEG having Mn 200, and two B blocks, each having a Mn of approximately 500 Da and containing 50 wt % ε-caprolacton and 50 wt % lactide. The end-group R is H in this case.

In cases where R is not H, the carbon chain length has been added to the formula.

For example PEG600(cap$_{50}$-lac$_{50}$)$_{2.0}$-06 indicates a RBABR triblock copolymer having an A-block consisting of PEG having a molecular weight (Mn) of 600, and two B-blocks each having a molecular weight (Mn) of approximately 600 (1200/2) and on each side a C6 R-group.

Experiment 1; Preparation of Copolymers.

A large number of RBABR copolymers have been prepared in accordance with the general synthesis procedure. Thermal properties and molecular weights have been determined. The results are listed in Table 1A and 1B.

TABLE 1A

Polymer synthesis

| # | Polymer composition | $M_{n, PCLA}$ | PCLA/PEG | CL/LA | Degree of modifycation | $M_{n, polymer}$ | PDI | $T_g$ (° C.) | $T_m$ (° C.) |
|---|---|---|---|---|---|---|---|---|---|
| 1 | PEG200(cap$_{50}$-lac$_{50}$)$_{5.0}$ | 1000 | 5.0 | 1 | — | 1337 | 1.27 | −45 | — |
| 2 | PEG200(cap$_{50}$-lac$_{50}$)$_{5.0}$-C3 | 1000 | 5.0 | 1 | 2 | 1453 | 1.23 | −45 | — |
| 3 | PEG200(cap$_{50}$-lac$_{50}$)$_{5.0}$-C6 | 1000 | 5.0 | 1 | 2 | 1518 | 1.23 | −51 | — |
| 4 | PEG200(cap$_{50}$-lac$_{50}$)$_{5.0}$-C12 | 1000 | 5.0 | 1 | 2 | 1570 | 1.23 | −53 | — |
| 5 | PEG200(cap$_{50}$-lac$_{50}$)$_{7.5}$ | 1500 | 7.5 | 1 | — | 1840 | 1.33 | −40 | — |
| 6 | PEG200(cap$_{50}$-lac$_{50}$)$_{7.5}$-C3 | 1500 | 7.5 | 1 | 2 | 1850 | 1.38 | −39 | — |
| 7 | PEG200(cap$_{50}$-lac$_{50}$)$_{7.5}$-C6 | 1500 | 7.5 | 1 | 2 | 1972 | 1.36 | −47 | — |
| 8 | PEG200(cap$_{50}$-lac$_{50}$)$_{10}$ | 2000 | 10 | 1 | — | 2659 | 1.37 | −37 | — |
| 9 | PEG200(cap$_{50}$-lac$_{50}$)$_{10}$-C3 | 2000 | 10 | 1 | 2 | 2275 | 1.50 | −36 | — |
| 10 | PEG200(cap$_{50}$-lac$_{50}$)$_{10}$-C6 | 2000 | 10 | 1 | 2 | 2493 | 1.44 | −40 | — |

TABLE 1A-continued

Polymer synthesis

| # | Polymer composition | $M_{n, PCLA}$ | PCLA/PEG | CL/LA | Degree of modifycation | $M_{n, polymer}$ | PDI | $T_g$ (° C.) | $T_m$ (° C.) |
|---|---|---|---|---|---|---|---|---|---|
| 11 | PEG600(cap$_{50}$-lac$_{50}$)$_{1.0}$ | 600 | 1.0 | 1 | — | 1206 | 1.10 | −57 | −5 |
| 12 | PEG600(cap$_{50}$-lac$_{50}$)$_{1.0}$-C3 | 600 | 1.0 | 1 | 2 | 1255 | 1.10 | −58 | −5 |
| 13 | PEG600(cap$_{50}$-lac$_{50}$)$_{1.0}$-C6 | 600 | 1.0 | 1 | 2 | 1387 | 1.09 | −63 | −8 |
| 14 | PEG600(cap$_{50}$-lac$_{50}$)$_{2.0}$ | 1200 | 2.0 | 1 | — | 1767 | 1.20 | −51 | — |
| 15 | PEG600(cap$_{50}$-lac$_{50}$)$_{2.0}$-C3 | 1200 | 2.0 | 1 | 2 | 1850 | 1.20 | −51 | — |
| 16 | PEG600(cap$_{50}$-lac$_{50}$)$_{2.0}$-C6 | 1200 | 2.0 | 1 | 2 | 1989 | 1.20 | −55 | — |
| 17 | PEG600(cap$_{50}$-lac$_{50}$)$_{4.0}$ | 2400 | 4.0 | 1 | — | 3254 | 1.32 | −40 | — |
| 18 | PEG600(cap$_{50}$-lac$_{50}$)$_{4.0}$-C3 | 2400 | 4.0 | 1 | 2 | 3432 | 1.31 | −40 | — |
| 19 | PEG600(cap$_{50}$-lac$_{50}$)$_{4.0}$-C6 | 2400 | 4.0 | 1 | 2 | 3182 | 1.36 | −45 | — |
| 20 | PEG1000(cap$_{50}$-lac$_{50}$)$_{0.5}$ | 500 | 0.5 | 1 | — | 1520 | 1.06 | −48 | 25 |
| 21 | PEG1000(cap$_{50}$-lac$_{50}$)$_{0.5}$-C3 | 500 | 0.5 | 1 | 2 | 1556 | 1.06 | −53 | 22 |
| 22 | PEG1000(cap$_{50}$-lac$_{50}$)$_{0.5}$-C6 | 500 | 0.5 | 1 | 2 | 1661 | 1.04 | −62 | 15 |
| 23 | PEG200(cap$_{75}$-lac$_{25}$)$_{5.0}$ | 1000 | 5.0 | 3 | — | 1422 | 1.26 | −62 | 1 |
| 24 | PEG200(cap$_{75}$-lac$_{25}$)$_{5.0}$-C3 | 1000 | 5.0 | 3 | 2 | 1487 | 1.27 | −61 | 1 |
| 25 | PEG200(cap$_{75}$-lac$_{25}$)$_{5.0}$-C6 | 1000 | 5.0 | 3 | 2 | 1688 | 1.24 | −66 | −8 |
| 26 | PEG200(cap$_{25}$-lac$_{75}$)$_{5.0}$ | 1000 | 5.0 | 0.33 | — | 1277 | 1.24 | −27 | — |
| 27 | PEG200(cap$_{25}$-lac$_{75}$)$_{5.0}$-C3 | 1000 | 5.0 | 0.33 | 2 | 1391 | 1.23 | −25 | — |
| 28 | PEG200(cap$_{25}$-lac$_{75}$)$_{5.0}$-C6 | 1000 | 5.0 | 0.33 | 2 | 1514 | 1.20 | −30 | — |
| 29 | PEG200(cap$_{75}$-lac$_{25}$)$_{7.5}$-C3 | 1500 | 7.5 | 3 | 2 | 1847 | 1.40 | N.A. | N.A. |
| 30 | PEG200(cap$_{75}$-lac$_{25}$)$_{7.5}$-C6 | 1500 | 7.5 | 3 | 2 | 2081 | 1.34 | N.A. | N.A. |

TABLE 2B

Polymer synthesis

| # | Polymer composition | $M_{n, PCLA}$ | PE/PEG | m/m | Degree of modification | $M_{n, polymer}$ | PDI | Tg (° C.) | Tm (° C.) |
|---|---|---|---|---|---|---|---|---|---|
| 31 | PEG200(cap$_{75}$-lac$_{25}$)$_{3.0}$-2-n-HD | 600 | 3.0 | 3 | 2 | 1333 | 1.13 | −60 | — |
| 32 | PEG200(cap$_{50}$-lac$_{50}$)$_{5.0}$-2-n-HD | 1000 | 5.0 | 1 | 2 | 1566 | 1.17 | −60 | — |
| 33 | PEG400(cap$_{60}$-lac$_{40}$)$_{5.0}$-succinic | 1000 | 5.0 | 1.5 | 2 | 2493 | 1.41 | −38 | — |
| 34 | PEG200(cap$_{40}$-gly$_{30}$-lac$_{30}$)$_{5.0}$-2-n-HD | 1000 | 5.0 | | 2 | 1707 | 1.16 | −42 | — |
| 35 | PEG200(cap$_{50}$-gly$_{50}$)$_{5.0}$-2-n-HD | 1000 | 5.0 | 1 | 2 | 1776 | 1.15 | −50 | — |
| 36 | PEG200(diox50-TMC50)5.0-2-n-HD | 1000 | 5.0 | 1 | 2 | 1844 | 1.20 | −50 | — |
| 37 | PEG200(cap$_{50}$-TMC$_{50}$)$_{5.0}$ | 1000 | 5.0 | 1 | 0 | 1676 | 1.55 | −59 | — |
| 38 | PEG200(cap$_{50}$-TMC$_{50}$)$_{5.0}$-C3 | 1000 | 5.0 | 1 | 2 | 1764 | 1.51 | −59 | — |
| 39 | PEG200(cap$_{50}$-TMC$_{50}$)$_{5.0}$-C6 | 1000 | 5.0 | 1 | 2 | 1910 | 1.47 | −62 | — |
| 40 | PEG200(cap$_{50}$-TMC$_{50}$)$_{5.0}$-C12 | 1000 | 5.0 | 1 | 2 | 2365 | 1.36 | −74 | −30 |
| 41 | PEG200(cap$_{50}$-TMC$_{50}$)$_{5.0}$-2-n-HD | 1000 | 5.0 | 1 | 2 | 1962 | 1.43 | −73 | — |
| 42 | PEG200(cap$_{50}$-val$_{50}$)$_{5.0}$ | 1000 | 5.0 | 1 | 0 | 1269 | 1.19 | −45 | 5 |
| 43 | PEG200(cap$_{50}$-val$_{50}$)$_{5.0}$-C3 | 1000 | 5.0 | 1 | 2 | 1670 | 1.27 | N.A. | N.A. |
| 44 | PEG200(cap$_{50}$-val$_{50}$)$_{5.0}$-C6 | 1000 | 5.0 | 1 | 2 | 1727 | 1.20 | −74 | 3 |
| 45 | PEG200(cap$_{50}$-val$_{50}$)$_{5.0}$-C12 | 1000 | 5.0 | 1 | 2 | 2223 | 1.28 | −74 | 2 |
| 46 | PEG200(cap$_{50}$-val$_{50}$)$_{5.0}$-2-n-HD | 1000 | 5.0 | 1 | 2 | 2028 | 1.25 | −74 | −1 |
| 47 | PEG200(cap$_{75}$-val$_{25}$)$_{5.0}$-C3 | 1000 | 5.0 | 3 | 2 | 1690 | 1.26 | −74 | 11 |
| 48 | PEG200(cap$_{75}$-val$_{25}$)$_{5.0}$-C6 | 1000 | 5.0 | 3 | 2 | 1985 | 1.24 | −62 | 12 |
| 49 | PEG200(cap$_{75}$-val$_{25}$)$_{5.0}$-C12 | 1000 | 5.0 | 3 | 2 | 2467 | 1.22 | — | 23 |
| 50 | PEG200(cap$_{75}$-lac$_{25}$)$_{5.0}$-2-n-HD | 1000 | 5.0 | 3 | 2 | 2197 | 1.11 | −63 | — |
| 51 | PEG200(cap$_{25}$-val$_{75}$)$_{5.0}$-C3 | 1000 | 5.0 | 1/3 | 2 | 1600 | 1.23 | −73 | 15 |
| 52 | PEG200(cap$_{25}$-val$_{75}$)$_{5.0}$-C6 | 1000 | 5.0 | 1/3 | 2 | 1707 | 1.24 | −75 | 14 |
| 53 | PEG200(cap$_{50}$-diox$_{50}$)$_{5.0}$ | 1000 | 5.0 | 1 | 0 | 1300 | 1.22 | −60 | — |
| 54 | PEG200(cap$_{50}$-diox$_{50}$)$_{5.0}$-C2 | 1000 | 5.0 | 1 | 2 | 1273 | 1.23 | −58 | — |
| 55 | PEG200(cap$_{50}$-diox$_{50}$)$_{5.0}$-C6 | 1000 | 5.0 | 1 | 2 | 1245 | 1.17 | −73 | −4 |
| 56 | PEG200(cap$_{50}$-diox$_{50}$)$_{5.0}$-C12 | 1000 | 5.0 | 1 | 2 | 1529 | 1.16 | −74 | −17 |
| 57 | PEG200(cap$_{50}$-diox$_{50}$)$_{5.0}$-2-n-HD | 1000 | 5.0 | 1 | 2 | 1608 | 1.17 | −73 | — |

In Table 1A and B PEG200, PEG600 and PEG1000 are polyethyleneglycol polymers with a molecular weight of respectively 200 g/mol, 600 g/mol and 1,000 g/mol.

$M_{n, PCLA}$ is the molecular weight of both B-blocks together, as calculated based on the molecular weight of the PEG A-block.

Cap is an abbreviation for ε-caprolactone.

Lac is an abbreviation for L-lactide, D-Lactide or DL-Lactide If not specifically mentioned, L-Lactide is chosen by default.

Gly is an abbreviation of glycolide

Diox is an abbreviation of p-dioxanone

TMC is an abbreviation of trimethylenecarbonate

Val is an abbreviation of δ-valerolactone

C3, C6 and C12 mean that the R-group comprises 3 (propionyl) respectively 6 (hexanoyl) or 12 (dodecanoyl) carbon atoms.

2-n-HD means that the R group contains an 2-n-hexyl-decanoyl endgroup.

$M_{n, polymer}$: Number-average molecular weight of PCLA block as determined with GPC PCLA/PEG: the ratio of PCLA to PEG
CL/LA: the ratio of ε-caprolactone to L-lactide
m/m: the ratio of the first monomer to the second monomer in the B block
PDI: polydispersity index according to GPC
$T_g$: glass transition temperature (midpoint) according to DSC
Tm: Melting temperature according to DSC
Degree of modification stands for number of aliphatic end-groups (R) after polymer modification. When the degree of modification is indicated as—, it means that R=H in the formula RBABR. When the degree of modification is 2, it means that R is a fatty acid residue comprising a number of C atoms.

Experiment 2; Testing of Polymers for Injectability.

The polymers listed in Tables 1A and B have been tested for injectability and viscosities have been measured at 20° C. and 37° C. Results are listed in Tables 2A and B.

TABLE 3A

Results injectability and rheology

| # | Polymer composition | Ejection time (seconds) at 20° C. 21 G (0.1 ml) | 25 G (0.1 ml) | 27 G (0.1 ml) | Viscosity (Pa · s) At 20° C. | At 37° C. |
|---|---|---|---|---|---|---|
| 1 | PEG200(cap$_{50}$-lac$_{50}$)$_{5.0}$ | 7 | 39 | >120 | 7.6 | 1.6 |
| 2 | PEG200(cap$_{50}$-lac$_{50}$)$_{5.0}$-C3 | 6 | 33 | >120 | 6.2 | 1.2 |
| 3 | PEG200(cap$_{50}$-lac$_{50}$)$_{5.0}$-C6 | 5 | 25 | >120 | 4.8 | 1.1 |
| 4 | PEG200(cap$_{50}$-lac$_{50}$)$_{5.0}$-C12 | 3 | 21 | >120 | 4.0 | 1.0 |
| 5 | PEG200(cap$_{50}$-lac$_{50}$)$_{7.5}$ | 20 | 100 | >120 | 19 | 3.0 |
| 6 | PEG200(cap$_{50}$-lac$_{50}$)$_{7.5}$-C3 | 12 | 80 | >120 | 16 | 3.2 |
| 7 | PEG200(cap$_{50}$-lac$_{50}$)$_{7.5}$-C6 | 10 | 48 | >120 | 7.3 | 2.4 |
| 8 | PEG200(cap$_{50}$-lac$_{50}$)$_{10}$ | 57 | >120 | Not ejectable* | 60 | 9.8 |
| 9 | PEG200(cap$_{50}$-lac$_{50}$)$_{10}$-C3 | 55 | >120 | Not ejectable* | 53 | 8.8 |
| 10 | PEG200(cap$_{50}$-lac$_{50}$)$_{10}$-C6 | 34 | >120 | Not ejectable* | 36 | 7.4 |
| 11 | PEG600(cap$_{50}$-lac$_{50}$)$_{1.0}$ | 1 | 6 | 23 | 1.3 | 0.4 |
| 12 | PEG600(cap$_{50}$-lac$_{50}$)$_{1.0}$-C3 | 1 | 5 | 17 | 0.9 | 0.3 |
| 13 | PEG600(cap$_{50}$-lac$_{50}$)$_{1.0}$-C6 | 1 | 5 | 16 | 0.5 | 0.3 |
| 14 | PEG600(cap$_{50}$-lac$_{50}$)$_{2.0}$ | 5 | 26 | >120 | 6.3 | 1.4 |
| 15 | PEG600(cap$_{50}$-lac$_{50}$)$_{2.0}$-C3 | 4 | 25 | >120 | 5.1 | 1.3 |
| 16 | PEG600(cap$_{50}$-lac$_{50}$)$_{2.0}$-C6 | 3 | 20 | >120 | 3.9 | 1.1 |
| 17 | PEG600(cap$_{50}$-lac$_{50}$)$_{4.0}$ | 43 | >120 | Not ejectable* | 56 | 10.3 |
| 18 | PEG600(cap$_{50}$-lac$_{50}$)$_{4.0}$-C3 | 37 | >120 | Not ejectable* | 36 | 9.2 |
| 19 | PEG600(cap$_{50}$-lac$_{50}$)$_{4.0}$-C6 | 29 | >120 | Not ejectable* | 33 | 7.2 |
| 20 | PEG1000(cap$_{50}$-lac$_{50}$)$_{0.5}$ | >120 | >120 | Not ejectable* | 117 | 0.4 |
| 21 | PEG1000(cap$_{50}$-lac$_{50}$)$_{0.5}$-C3 | 1 | 5 | 52 | 2.0 | 0.3 |
| 22 | PEG1000(cap$_{50}$-lac$_{50}$)$_{0.5}$-C6 | 1 | 4 | 16 | 3.2 | 0.3 |
| 23 | PEG200(cap$_{75}$-lac$_{25}$)$_{5.0}$ | 1 | 9 | 34 | 1.9 | 0.6 |
| 24 | PEG200(cap$_{75}$-lac$_{25}$)$_{5.0}$-C3 | 1 | 7 | 27 | 1.8 | 0.6 |
| 25 | PEG200(cap$_{75}$-lac$_{25}$)$_{5.0}$-C6 | 1 | 6 | 24 | 1.6 | 0.4 |
| 26 | PEG200(cap$_{25}$-lac$_{75}$)$_{5.0}$ | >120 | >120 | Not ejectable* | 92 | 7.7 |
| 27 | PEG200(cap$_{25}$-lac$_{75}$)$_{5.0}$-C3 | 50 | >120 | Not ejectable* | 61 | 6.6 |
| 28 | PEG200(cap$_{25}$-lac$_{75}$)$_{5.0}$-C6 | 33 | >120 | Not ejectable* | 38 | 5.0 |
| 29 | PEG200(cap$_{75}$-lac$_{25}$)$_{7.5}$-C3 | 4 | 24 | >120 | 4.3 | N.A. |
| 30 | PEG200(cap$_{75}$-lac$_{25}$)$_{7.5}$-C6 | 2 | 16 | >120 | 2.8 | N.A. |

*not ejectable: no polymer was observed at the tip of the needle during the experiment.

TABLE 4B

Results injectability and rheology

| # | Polymer composition | Ejection time (seconds) at 20° C. 21 G (0.1 ml) | 25 G (0.1 ml) | 27 G (0.1 ml) | Viscosity (Pa · s) At 20° C. | At 37° C. |
|---|---|---|---|---|---|---|
| 31 | PEG200(cap$_{75}$-lac$_{25}$)$_{3.0}$-HD | 2 | 10 | <120 | 1.7 | 0.50 |
| 32 | PEG200(cap$_{50}$-lac$_{50}$)$_{5.0}$-HD | 3 | 13 | 50 | 2.3 | 0.63 |
| 33 | PEG400(cap$_{60}$-lac$_{40}$)$_{5.0}$-succinic | 54 | N.A. | N.A. | 93 | 15 |
| 34 | PEG200(cap$_{40}$-gly$_{30}$-lac$_{30}$)$_{5.0}$-HD | 24 | 41 | N.A. | 27.9 | 4.7 |
| 35 | PEG200(cap$_{50}$-gly$_{50}$)$_{5.0}$-HD | 11 | 41 | N.A. | 11.9 | 2.6 |
| 36 | PEG200(diox50-TMC50)5.0-HD | 21 | 41 | N.A. | 27 | 4.8 |
| 37 | PEG200(cap$_{50}$-TMC$_{50}$)$_{5.0}$ | 9 | N.A. | N.A. | 10 | 2.8 |
| 38 | PEG200(cap$_{50}$-TMC$_{50}$)$_{5.0}$-C3 | 6 | N.A. | N.A. | 6.6 | 1.9 |
| 39 | PEG200(cap$_{50}$-TMC$_{50}$)$_{5.0}$-C6 | 6 | N.A. | N.A. | 5.9 | 1.8 |
| 40 | PEG200(cap$_{50}$-TMC$_{50}$)$_{5.0}$-C12 | 6 | N.A. | N.A. | 6.7 | 2.1 |
| 41 | PEG200(cap$_{50}$-TMC$_{50}$)$_{5.0}$-HD | 3 | 13 | 51 | 2.7 | 0.82 |
| 42 | PEG200(cap$_{50}$-val$_{50}$)$_{5.0}$ | 1 | 4 | 11 | 0.43 | 0.18 |
| 43 | PEG200(cap$_{50}$-val$_{50}$)$_{5.0}$-C3 | 2 | 7 | 23 | 1.0 | 0.40 |
| 44 | PEG200(cap$_{50}$-val$_{50}$)$_{5.0}$-C6 | 1 | 5 | 21 | 1.0 | 0.40 |
| 45 | PEG200(cap$_{50}$-val$_{50}$)$_{5.0}$-C12 | 2 | 10 | N.A. | 1.8 | 0.70 |
| 46 | PEG200(cap$_{50}$-val$_{50}$)$_{5.0}$-HD | 2 | 12 | N.A. | 2.2 | 0.80 |
| 47 | PEG200(cap$_{75}$-val$_{25}$)$_{5.0}$-C3 | 1 | 8 | N.A. | 1.8 | 0.53 |

TABLE 4B-continued

Results injectability and rheology

| | | Ejection time (seconds) at 20° C. | | | Viscosity (Pa · s) | |
|---|---|---|---|---|---|---|
| # | Polymer composition | 21 G (0.1 ml) | 25 G (0.1 ml) | 27 G (0.1 ml) | At 20° C. | At 37° C. |
| 48 | PEG200(cap$_{75}$-val$_{25}$)$_{5.0}$-C6 | 2 | 9 | N.A. | 2.5 | 0.58 |
| 49 | PEG200(cap$_{75}$-val$_{25}$)$_{5.0}$-C12 | Not eject | N.A. | N.A. | 16 | 0.83 |
| 50 | PEG200(cap$_{75}$-lac$_{25}$)$_{5.0}$-HD | 4 | 23 | 41 | 3.9 | 1.2 |
| 51 | PEG200(cap$_{25}$-val$_{75}$)$_{5.0}$-C3 | 2 | 8 | N.A. | 2.0 | 0.51 |
| 52 | PEG200(cap$_{25}$-val$_{75}$)$_{5.0}$-C6 | 1 | 7 | N.A. | 1.8 | 0.52 |
| 53 | PEG200(cap$_{50}$-diox$_{50}$)$_{5.0}$ | 2 | 11 | 46 | 2.1 | 0.63 |
| 54 | PEG200(cap$_{50}$-diox$_{50}$)$_{5.0}$-C2 | 2 | 11 | 43 | 2.1 | 0.62 |
| 55 | PEG200(cap$_{50}$-diox$_{50}$)$_{5.0}$-C6 | 1 | 3 | 12 | 0.62 | 0.23 |
| 56 | PEG200(cap$_{50}$-diox$_{50}$)$_{5.0}$-C12 | 1 | 5 | 20 | 0.87 | 0.32 |
| 57 | PEG200(cap$_{50}$-diox$_{50}$)$_{5.0}$-HD | 1 | 8 | 23 | 1.0 | 0.34 |

A second set of polymers was prepared using monomers with a low Tg and Tm (melting point) in combination with ε-caprolactone (see also table 1B). The combination of ε-caprolactone with for example dioxanone or δ-valerolactone gives low viscous and excellent injectable copolymers.

Large differences were observed in ejection times depending on the total polymer molecular weight and the molecular composition. As shown in Table 2, the end-group (C6 or C12) had a significant effect on the ejection time. In general, polymers with end-group R=H show a low ejectability and relatively high viscosity. C3-endcapped polymers had better ejectability properties and C6 or C12 modified polymers had the best ejectability properties and the lowest viscosity, compared to unmodified ones (with R=H).

The composition of the PCLA-block (B-block) is also of great importance. For example: a polymer with a composition of PEG200(cap$_{25}$-lac$_{75}$)$_{5.0}$-C3 was not ejectable, while changing the composition to PEG200(cap$_{75}$-lac$_{25}$)$_{5.0}$-C3 resulted in a very nice ejectable polymer. The viscosity is dropping when caprolactone is the major component of the PCLA-block. The inventors believe that this has to do with the lower T$_g$ of caprolactatee monomer units compared to the more rigid lactate monomer units. Increasing the temperature to 37° C. results in less viscous polymers. Ejections at 37° C. are much easier and significantly lower the ejection time for these polymers.

As shown in Table 1 the thermal properties of the polymers were determined using DSC. Polymers composed with PEG1000 have a melting temperature around 20° C. These polymers crystallize in the refrigerator (4° C.) and even at ambient temperature. End-capping these polymers lowers the melting temperature, but not low enough to prevent crystallization. However, the copolymers may be warmed up to 37° C. prior to injection to 'melt' the crystalline domains of the PEG. If preferred, said copolymers may be cooled to room temperature again prior to injection without immediate crystallization happens and with that without immediate increase in viscosity.

Figure 2:
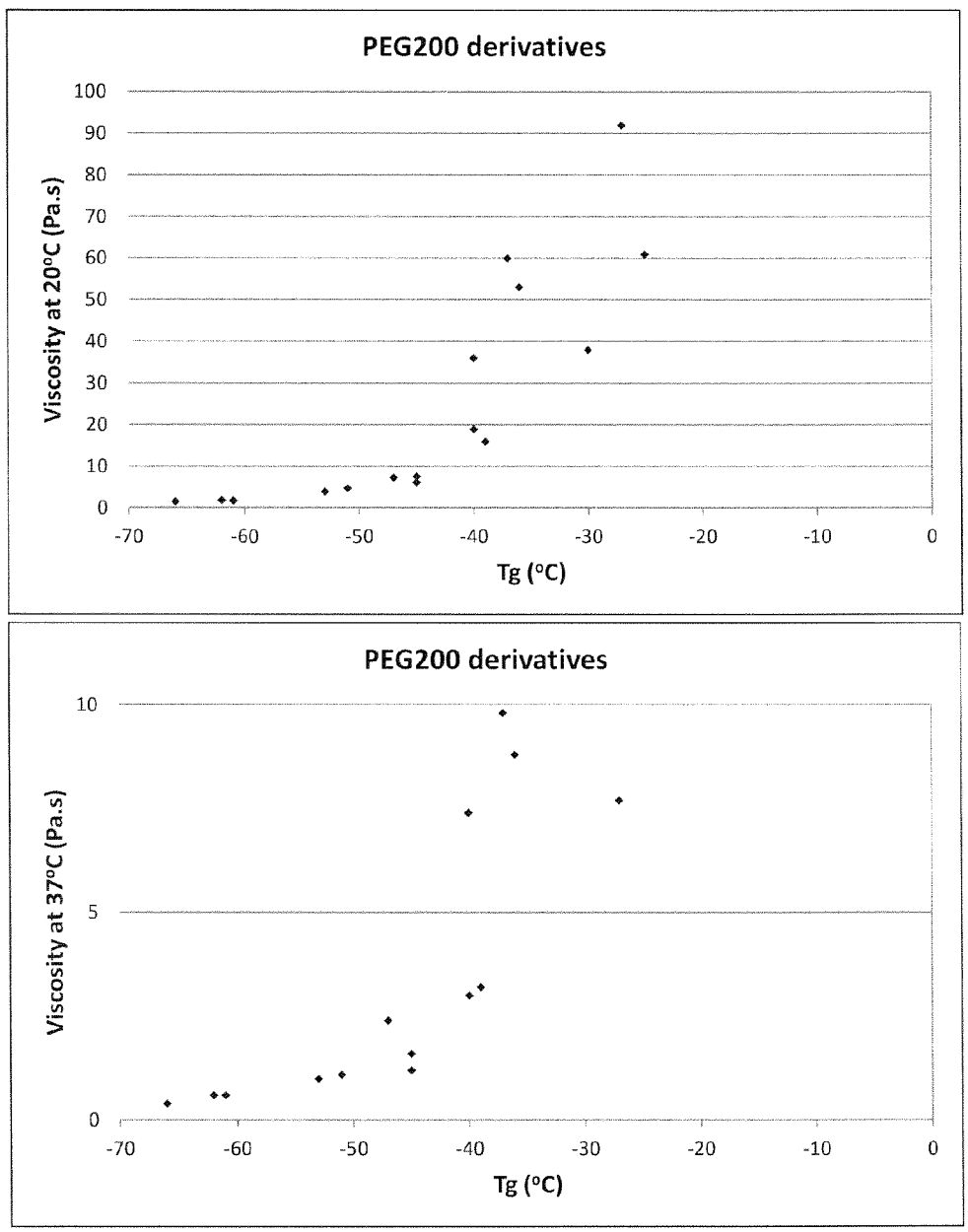
FIG. 2 shows the viscosity of various PEG200 derivatives at 20° C. and 37° C. versus the $T_g$ (° C.).

The relation between the glass transition temperature (T$_g$) and the viscosity of PEG200-derivatives is shown in FIG. 2. The lower the T$_g$ the lower the viscosity of the polymer. If the T$_g$ is lower than approx. -40° C. the polymers can be ejected through a thin needle of ≤25 G. A higher T$_g$ results in a higher viscosity and with that a worse ejectability. This may be circumvented by choosing for a higher ejection temperature (e.g. 37° C.) as is shown in FIG. 2, as well.

Figure 3:
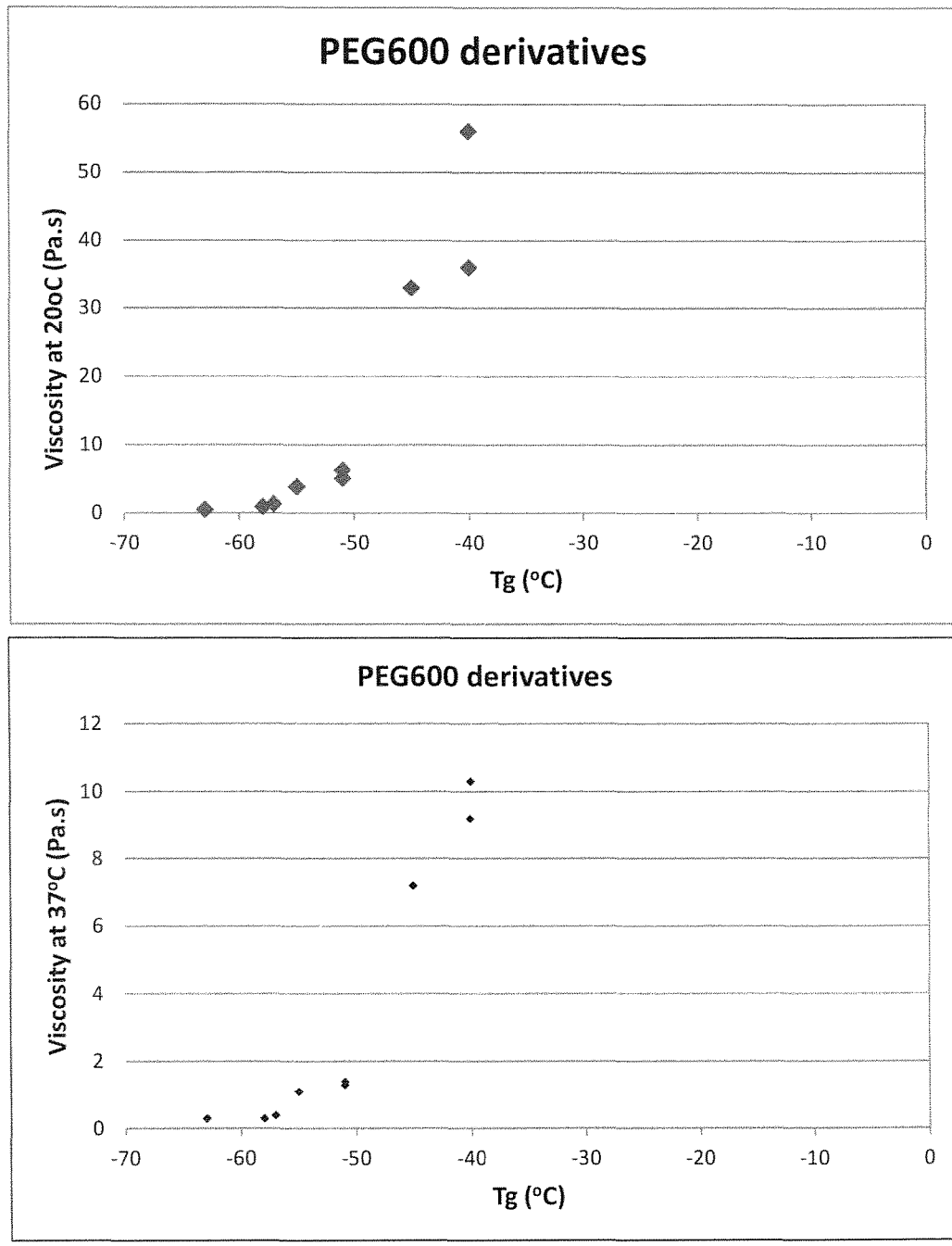
FIG. 3 shows the viscosity of various PEG600 derivatives at 20° C. and 37° C. versus the $T_g$ (° C.).

The same trend is observed for the PEG600-derivatives (FIG. 3). Only the T$_g$ of these polymers should be lower than approx. -50° C. to allow ejection through a thin needle of ≤25 G at 20° C.

Experiment 3: In-Vitro Release of Lidocaïne-HCl

A selection of polymers were loaded with 1% lidocaïne-HCl (small hydrophilic API). A known amount of loaded polymer (250-350 mg) was transferred into small tubes (15 ml), followed by the addition of 5 mL PBS (pH=7.4; 52 mm; 300 mOsm; pre-warmed at 37° C.). The tubes were placed in a shaking incubator at 37° C.

Release samples were taken during 7 days, at these time points buffer (600 μl) was removed from the supernatant and replaced by pre-warmed PBS. The samples were analysed for its lidocaine content using UHPLC.

Figure 4:
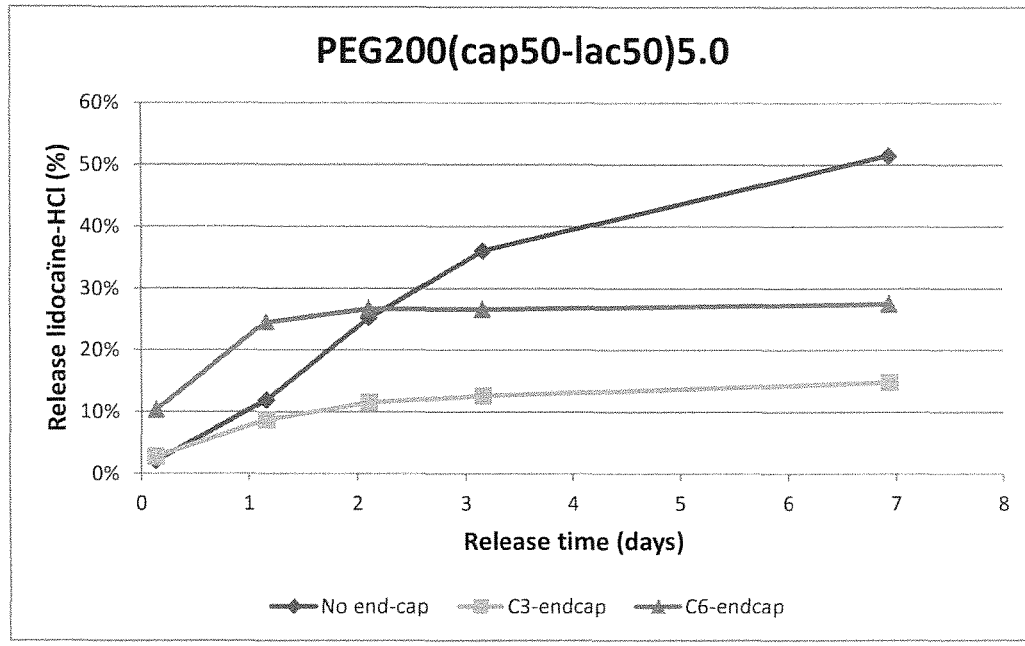
FIG. 4 shows the cumulative release (%) of lidocaine-HCl versus the release time (days) for the release of lidocaine-HCl from PEG200(cap50-lac50)5.0.

In the first day small differences were observed between the three different polymers, composition PEG200(cap$_{50}$-lac$_{50}$)$_{5.0}$ (FIG. 4). The effect of an end-group was becoming more clear after 2 days. After 7 days the polymer with no end-group (R=H) showed a release of approx. 51%. Slower release of lidocaïne-HCl was observed with end-groups. A C3-end-group showed a release of approx. 28% and a C6-end-group showed a release of approx. 15% after 7 days.

Figure 5:
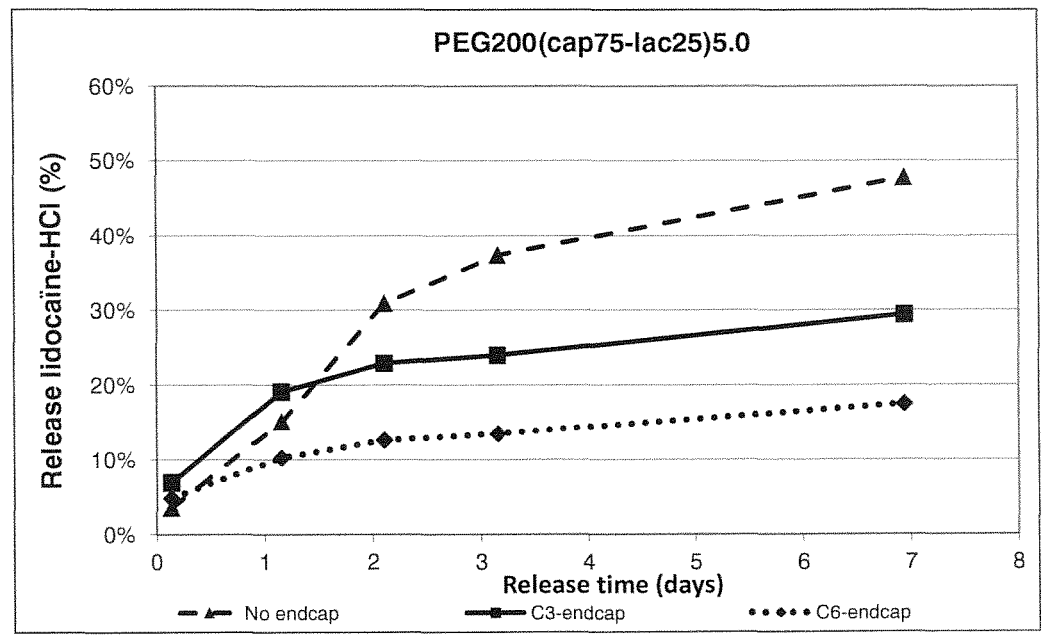
FIG. 5 shows the cumulative release (%) of lidocaine-HCl versus the release time (days) for the release of lidocaine-HCl from PEG200(cap75-lac25)5.0.

As shown in FIG. 5 similar results were obtained with polymers with composition PEG200(cap$_{75}$-lac$_{25}$)$_{5.0}$, whereas the polymer with no end-group (R=H) showed a lidocaïne-HCl release of approx. 47% after 7 days. The C3-endcapped showed a release of approx. 30%, a greater effect on the release was observed with the C6-endcapped polymer, which gave a release of approx. 18% after 7 days.

Figure 6:
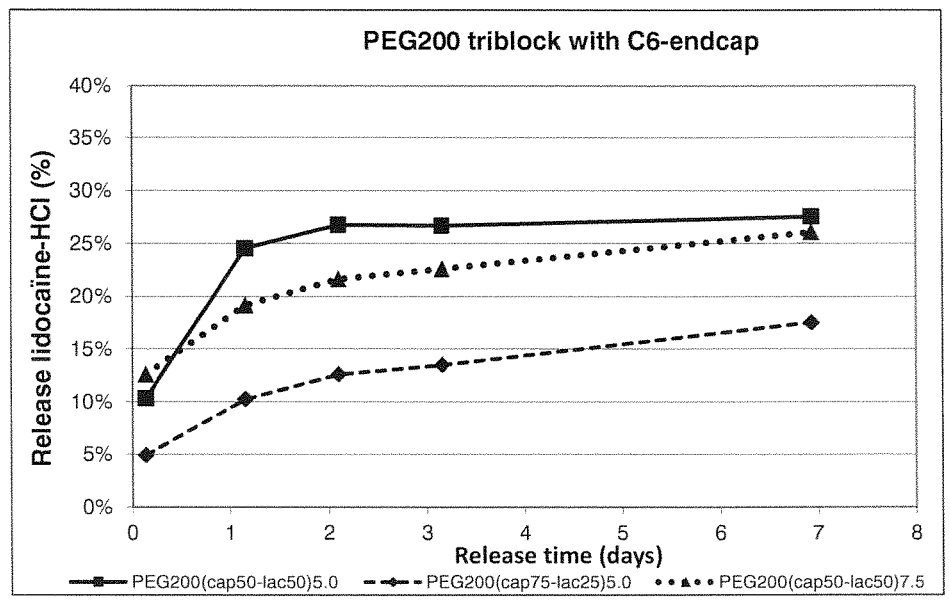
FIG. 6 shows the cumulative release (%) of lidocaine-HCl versus the release time (days) for the release of lidocaine-HCl from three different PEG200 block copolymers with a C6 end-group.

Besides the influence of the end-groups on the release of lidocaïne-HCl also the effect of the polyester block length and monomer composition was determined (FIG. 6). In this experiment three polymers based on PEG200 with C6 end-groups but with different polyester block length or PCLA-ratio were compared. By varying these parameters small differences in release were observed. After 7 days approx. 18%-28% of lidocaine-HCl was released.

Figure 7:
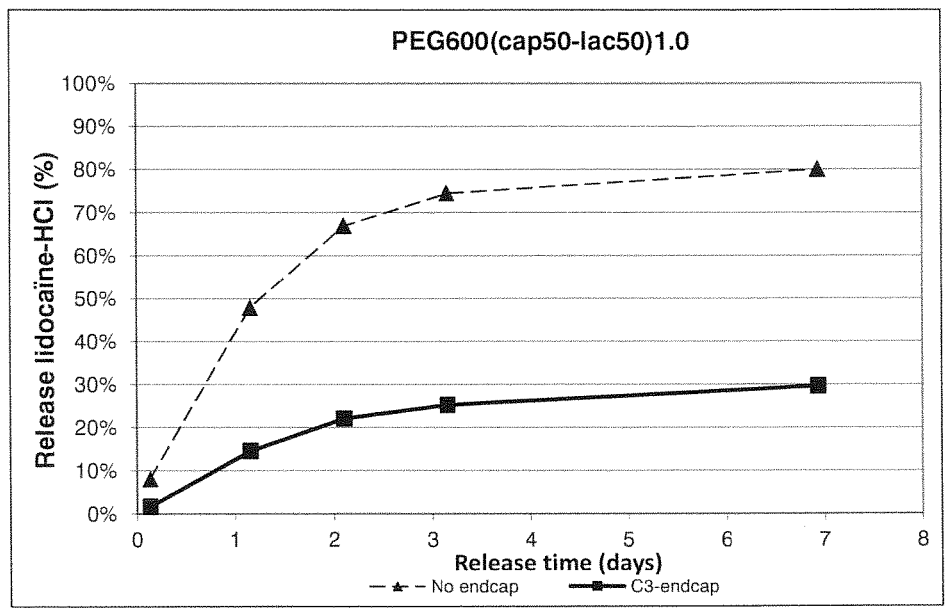
FIG. 7 shows the cumulative release (%) of lidocaine-HCl versus the release time (days) for the release of lidocaine-HCl from PEG600(cap50-lac50)1.0.

The positive effect (=slower release) of the end-group was even more clear with polymer PEG600(cap$_{50}$-lac$_{50}$)1.0. No end-group (R=H) resulted in the release of 80% lidocaïne-HCl after 7 days, whereas the C3-endcapped version shows a release of 30% after 7 days (FIG. 7).

Experiment 4: In-Vitro Release of Lysozyme

Polymers were selected and loaded with 10% lysozyme. A known amount of loaded polymer (between the 250-350 mg of the loaded liquid polymer) was transferred into small tubes (15 ml), followed by the addition of 3 ml PBS (pH=7.4; 52 mm; 300 mOsm; pre-warmed at 37° C.). The tubes were placed in a shaking incubator at 37° C.

Release samples were taken during 7 days, at these time points buffer (300 μl) was removed from the supernatant and analysed for lysozyme release using a BCA protein assay.

Directly after sampling pre-warmed fresh PBS (300 μl) was added to continue the release study.

Figure 8:
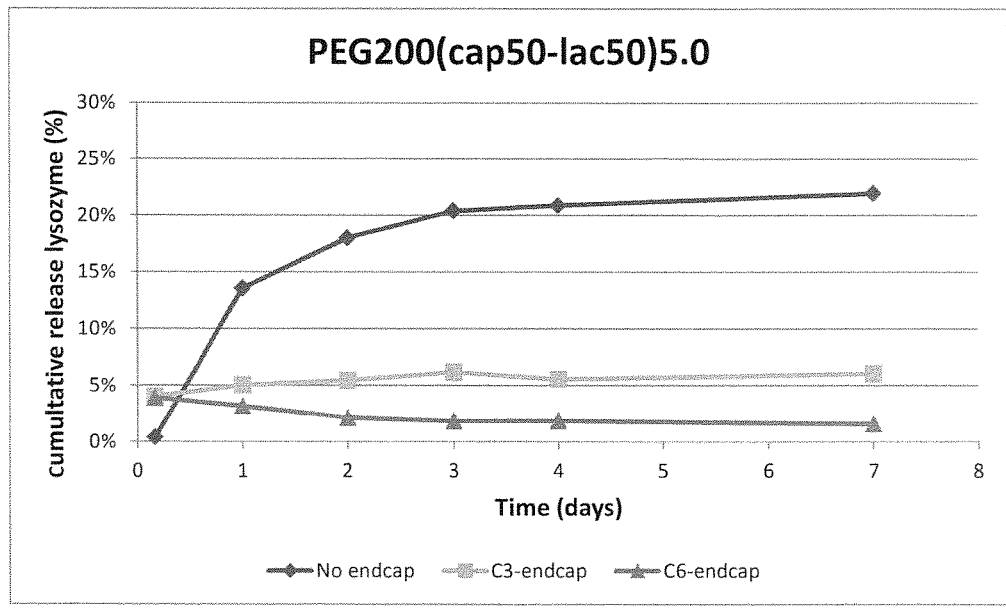
FIG. 8 shows the cumulative release (%) of lysozyme versus the release time (days) for the release of lysozyme from PEG200(cap50-lac50)5.0.

FIG. 8 illustrates that during the first 3 days lysozyme was released much faster from the non-end-capped polymer PEG200(cap50-lac50)5.0 compared to the end-capped versions of the same polymer composition. After 3 days the release slows down for all formulations. This example demonstrates the beneficial effect of the end-group on reducing the burst release.

Figure 9:
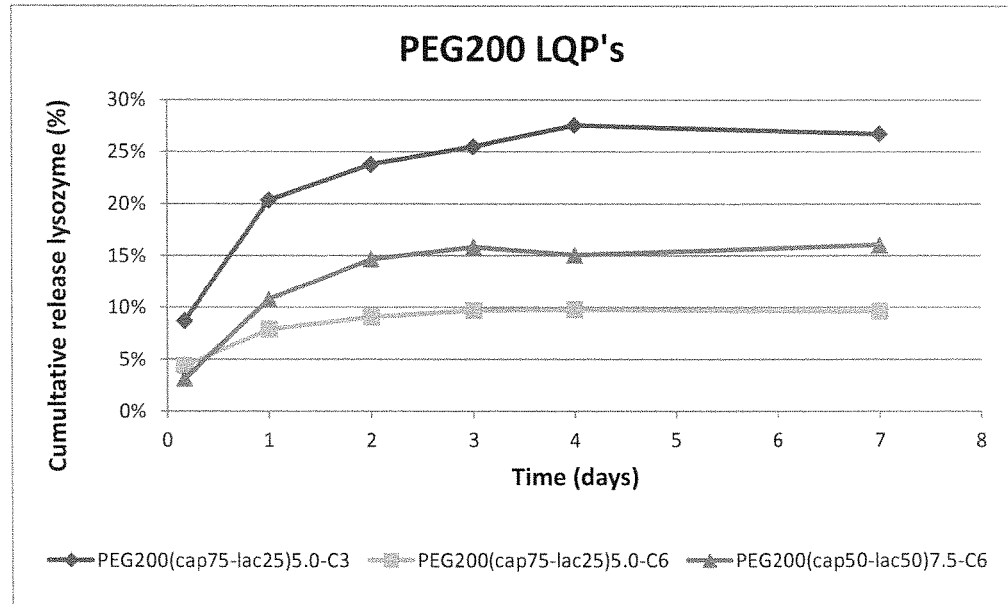
FIG. 9 shows the cumulative release (%) of lysozyme versus the release time (days) for the release of lysozyme from three different PEG200 block copolymers.

FIG. 9 shows that a longer end-group gives more retention of lysozyme release. Polymer PEG200(cap50-lac50)7.5-C6 is a more viscous polymer (higher molecular weight), this also can provide more retention.

Figure 10:
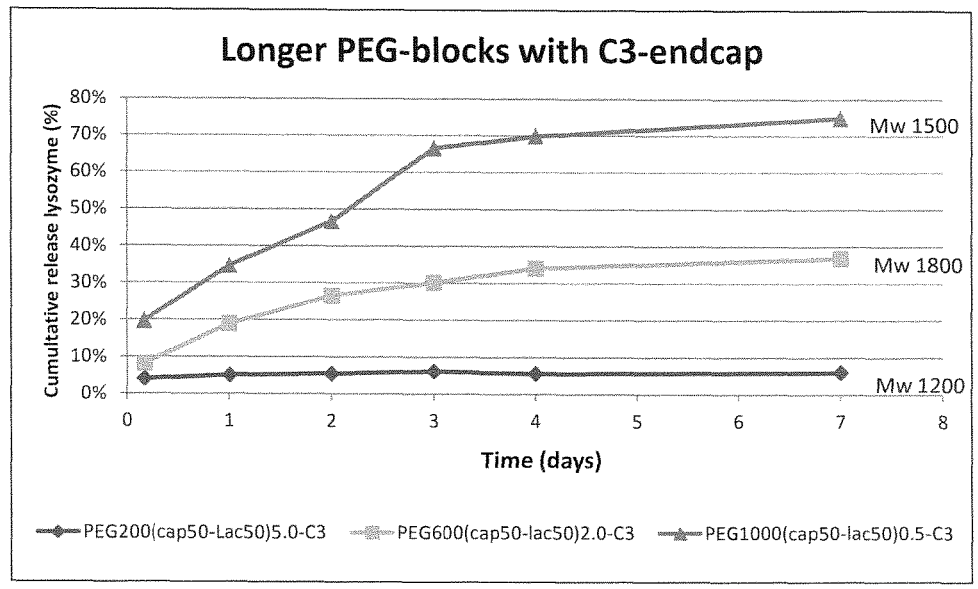
FIG. 10 shows the cumulative release (%) of lysozyme versus the release time (days) for the release of lysozyme from three different PEG200 block copolymers with a C3 end-group.
Figure 11:
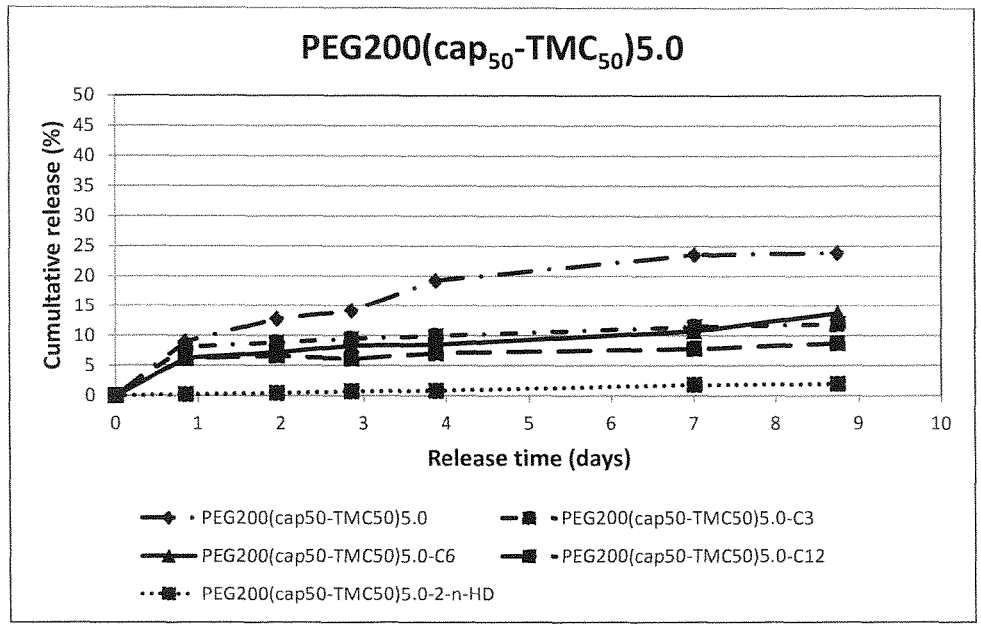
FIG. 11 is another example of what the effect is of an end-group on the in vitro release results using the PEG200 (cap50-TMC50) 5.0 matrix. Slight differences were observed after 24 hours. After 7 days the effect of the end-group could be seen. After 7 days the copolymer with R=H showed a lidocaine-HCl release of approx. 24%. The C3-endcapped showed a release of approx. 11%, a greater effect had the branched end-group with a release of approx. 2% after 7 days.
Figure 12:
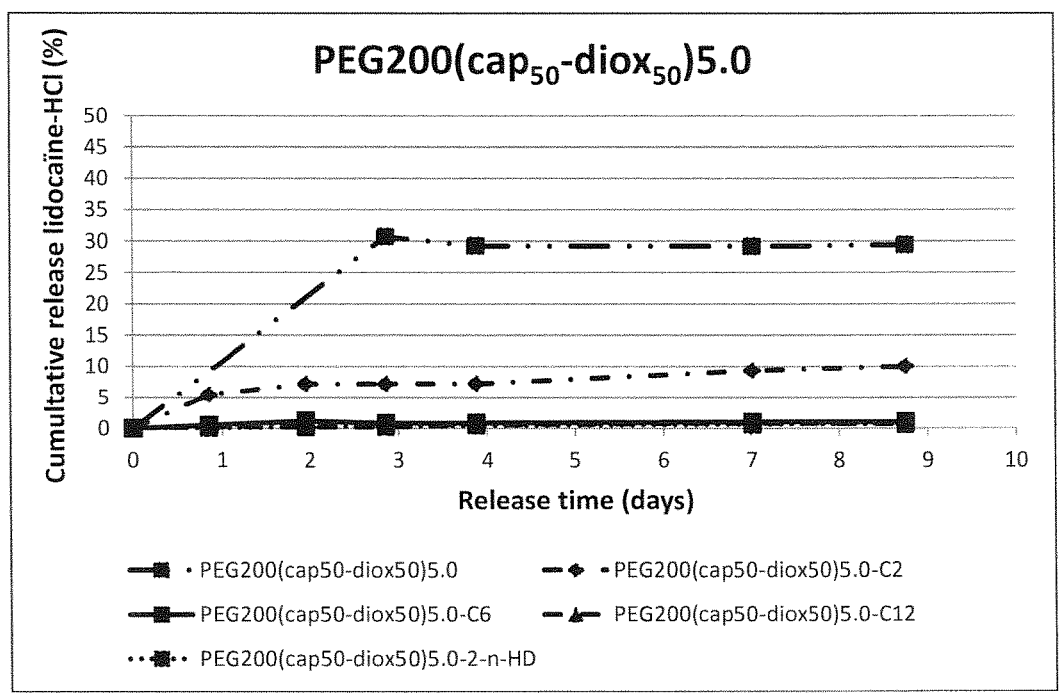
FIG. 12 shows the effect of an end-group on the in vitro release results using the PEG200(cap$_{50}$-diox$_{50}$)$_{5.0}$ matrix. Big differences were observed after 24 hours. The non-endcapped copolymer showed a lidocaine-HCl release of approx. 40% in 24 hours. Whereas the endcapped copolymers showed releases between the 0% and 6%. Even after 7 days almost no lidocaine-HCl was release from the copolymers with big endgroups (R=C6, C12 or 2-n-HD).

Not only the composition of the PCLA-block or the molecular weight of the polymer is of great importance to control the release properties, but, as shown in FIG. 10, also the hydrophilic part (PEG block) has a huge effect. Longer PEG blocks give faster release in comparison to polymers with molecular weights in the same range and same PCLA composition.

Experiment 5: Ex-Vivo Injection of Copolymer.

Polymers were injected in a rat cadaver at 37° C. (rats were sacrificed 1 minute before injection; the rats were taken from another study and not sacrificed for the purpose of the injection studies). The polymers were loaded with a trace of methylene blue for better visualization. Immediately after injection, the skin of the rat was removed. To our surprise, a nice "gummy" depot was formed. Depots were retrieved and stored at room temperature. After 10 weeks the depots were still "gummy".

Experiment 6: Determination of Viscosities of Pharmaceutical Compositions

A new set of liquid polymers was synthesised to measure the effect on the viscosity when these were loaded (1% w/w) with an API (lidocaine, lidocaine-HCl, Celecoxib or lysozyme). First a vial was charged with an known amount of polymer, followed by the addition of the appropriate API. The vials were stored at 37° C. for a few hours. In this time the API's dissolved into the polymer matrix, after which the samples were mixed using a spatula. Before measuring the viscosity (single measurement using the method as previous described), the samples were stored under ambient conditions for at least 24 hours. As depicted in Table 5, loading the polymers with 1% (w/w) API had not a significant effect on the viscosity.

TABLE 5

Viscosity (Pa · s) of polymers, at 20° C., with or without API (1% w/w)

| # | Polymer composition | No API | Lidocaine-HCl | Lidocaine | Celecoxib | Lysozyme |
|---|---|---|---|---|---|---|
| 1 | PEG200(cap$_{50}$-lac$_{50}$)$_{5.0}$ | 8.4 | 8.6 | 8.4 | 8.5 | 7.7 |
| 2 | PEG200(cap$_{50}$-lac$_{50}$)$_{5.0}$-C3 | 6.4 | 6.0 | 6.4 | 7.0 | 6.0 |
| 3 | PEG200(cap$_{50}$-lac$_{50}$)$_{5.0}$-C6 | 4.0 | 3.7 | 3.8 | 4.4 | 3.9 |
| 11 | PEG600(cap$_{50}$-lac$_{50}$)$_{1.0}$ | 1.3 | 1.4 | 1.3 | N.A. | 1.2 |
| 12 | PEG600(cap$_{50}$-lac$_{50}$)$_{1.0}$-C3 | 1.0 | 1.0 | 1.0 | 1.0 | 1.0 |
| 15 | PEG600(cap$_{50}$-lac$_{50}$)$_{2.0}$-C3 | 5.1 | 5.3 | 5.0 | N.A. | 5.2 |
| 23 | PEG200(cap$_{75}$-lac$_{25}$)$_{5.0}$ | 1.9 | 2.1 | 1.9 | 2.0 | 1.7 |
| 24 | PEG200(cap$_{75}$-lac$_{25}$)$_{5.0}$-C3 | 1.8 | 1.6 | 1.5 | 1.6 | 1.7 |
| 25 | PEG200(cap$_{75}$-lac$_{25}$)$_{5.0}$-C6 | 1.6 | 1.5 | 1.5 | N.A. | 1.5 |

Experiment 7.

Different examples of RBABR copolymers have been prepared, and the thermal properties as well as viscosities have been determined.

In all cases PEG is used as the A block. The B block has been varied with a combination of 1 to 3 different monomers from the group of monomers as depicted below:

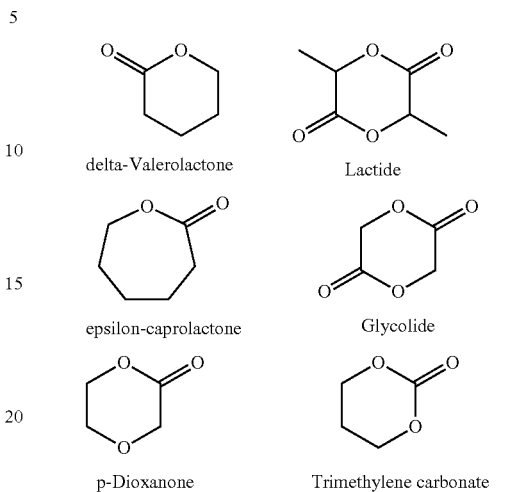

delta-Valerolactone  Lactide epsilon-caprolactone  Glycolide p-Dioxanone  Trimethylene carbonate Table 4 summarizes the thermal properties of the homopolymers of these monomers.

TABLE 6

Properties of homopolymers

| | Tg (° C.) | Tm (° C.) |
|---|---|---|
| ε-Caprolactone | −60 | 60 |
| Lactide | 60 | 175 |
| p-Dioxanone | −10-0 | 110 |
| Glycolide | 35-40 | 225-230 |
| δ-Valerolactone | −67 | 60 |
| Trimethylene carbonate | −26--15 | 36 |

Table 4 shows that the monomers ε-caprolactone and δ-valerolactone will support the beneficial thermal properties of the RBABR copolymers, and also p-dioxanone and trimethylene carbonate have reasonable low $T_g$ values. At the same time it is important to avoid the formation of crystalline domains in the RBABR copolymer. Large amounts of lactide and glycolide should be avoided due to the rigid structure of these monomers as demonstrated by the high Tg and Tm values of the homopolymers.

The thermal properties of the A block are also of important. In case the A block is PEG the following relation between mol weight and melting point can be found (table 5):

TABLE 7

Melting points of PEG

| Polyethylene glycol mol weight | Melting point (° C.) |
|---|---|
| 200 | −65 |
| 600 | 17-22 |
| 1000 | 35-40 |
| 1250 | 40-45 |

TABLE 8

Viscosity properties using other monomers

| # | Polymer composition | Viscosity (Pa·s) At 20° C. | Viscosity (Pa·s) At 37° C. | Thermal properties Tg (° C.) | Thermal properties Tm (° C.) |
|---|---|---|---|---|---|
| 58 | PEG200(cap)$_{1.0}$ | 0.46 | 0.09 | −80 | 19 |
| 59 | PEG200(cap)$_{1.0}$-C3 | 0.16 | 0.13 | −81 | 20 |
| 60 | PEG200(cap)$_{5.0}$ | N.A.* | N.A.* | −77 | 40 |
| 61 | PEG200(cap)$_{5.0}$-C6 | N.A.* | N.A.* | — | 44 |
| 62 | PEG200(DL-lactide)$_{5.0}$ | N.A.* | 101 | −6 | — |
| 63 | PEG600(DL-lactide)$_{1.0}$ | 7.2 | 1.3 | −40 | — |
| 64 | PEG600(DL-lactide)$_{2.0}$ | 289 | 19.2 | −25 | — |
| 65 | PEG200(cap$_{75}$-gly$_{25}$)$_{5.0}$ | 3.7 | 1.0 | −57 | — |
| 66 | PEG200(cap$_{50}$-gly$_{50}$)$_{5.0}$ | 26.3 | 5.8 | −41 | — |
| 67 | PEG200(gly$_{50}$-lac$_{50}$)$_{5.0}$ | N.A.* | N.A.* | −25 | — |
| 68 | PEG200(valero$_{50}$-lac$_{50}$)$_{5.0}$ | 7.0 | 1.5 | −44 | — |
| 69 | PEG200(cap$_{40}$-lac$_{30}$-gly$_{30}$)$_{5.0}$ | 21.8 | 3.6 | −34 | — |
| 70 | PEG200(cap$_{40}$-lac$_{30}$-gly$_{30}$)$_{5.0}$-C6 | 12 | 2.3 | −42 | — |
| 71 | PEG200(cap$_{25}$-diox$_{75}$)$_{5.0}$ | 0.7 | 0.2 | Not measured | Not measured |
| 72 | PEG200(cap$_{25}$-diox$_{75}$)$_{5.0}$-C6 | 0.4 | 0.2 | Not measured | Not measured |
| 73 | PEG200(cap$_{50}$-diox$_{50}$)$_{5.0}$ | 2.0 | 0.7 | Not measured | Not measured |
| 74 | PEG200(cap$_{50}$-diox$_{50}$)$_{5.0}$-C6 | 0.7 | 0.3 | Not measured | Not measured |
| 75 | PEG200(cap$_{75}$-diox$_{25}$)$_{5.0}$ | 1.6 | 0.6 | Not measured | Not measured |
| 76 | PEG200(cap$_{75}$-diox$_{25}$)$_{5.0}$-C6 | 0.8 | 0.3 | Not measured | Not measured |

*Not available, not able to suck up the polymer with a syringe (without needle).

Using only ε-caprolactone as hydrophobic component results in a very liquid polymer with a low T$_g$ (≠−80° C.) at ambient temperature. Storage in the fridge solidifies the polymer due to its higher melting temperature. The polymers with only DL-lactide (50/50 D/L ratio) have a high viscosity due to their relatively high T$_g$ varying from −6 to −40° C.

Two polymers were made with PEG200, ε-caprolactone and glycolide with different composition of the hydrophobic block, a higher amount (75%) of ε-caprolactone reduces the T$_g$ and thus lowers the viscosity. A combination of glycolide and lactide as hydrophobic block is not a good match due to the high T$_g$ of both monomers (see table 4) and gives a very viscous, almost solid polymer.

Another monomer with a low Tg (δ-valerolactone) was introduced, this in combination with lactide and PEG200 resulted in a polymer with relatively low viscosity. This polymer is comparable with PEG200(cap$_{50}$-lac$_{50}$)$_{5.0}$, due to the lower T$_g$ of δ-valerolactone the viscosity of this polymer is slightly lower.

Also a combination of three monomers is possible (PEG200(cap$_{40}$-lac$_{30}$-gly$_{30}$)$_{5.0}$). Chemical modification to a C6-endgroup reduces the T$_g$ and the viscosity.

It has been found that a combination of two monomers in the B block that have a low Tg gives RBABR block copolymers having a low viscosity and excellent injectability. For example the use of ε-caprolactone and dioxanon as monomeric units for the B-block gives excellent RBABR block copolymers (see samples 44-49).

Experiment 8; State of the Art Polymers

A number of state of the art polymers have been prepared from different prior art references. The viscosity of the neat polymers has been measured at 20° C.

TABLE 7 viscosities of prior art copolymers.

| Reference | Polymer | Mean visco at 20° C. (Pa·s) |
|---|---|---|
| EP2343046; example 1 | PEG1500(L-Lac$_{50}$-TMC$_{50}$)1.2 | >4000 |
| U.S. Pat. No. 7,740,877B2: example 2 | PEG1500(Cap$_{50}$-L-Lac$_{50}$)1.2-C6 | 141 |
| WO2012/131104: example 1 | PEG1500(cap$_{90}$-lac$_{10}$)$_{2.2}$-C2 | >2000000 |
| Angew. Chem. Int. Ed. 2006, 45, 2232-2235: example B | PEG1000(DL-lac$_{67}$-Gly$_{33}$)1.8-C2 | 3090 |

All polymers show crystallinity, and have a melting temperature above 20° C. In order to be able to measure viscosity at 20° C., the samples have been melted first at 50° C., and subsequently cooled down to 20° C. After 4 minutes conditioning at 20° C., the viscosity has been measured of the samples. The sample from EP2343046 and WO2012/131104 crystallized during the measurement and give very high viscosity values.

All samples have high viscosities relative to the BAB block copolymers according to the invention.

What is claimed is:

1. A bioresorbable triblock copolymer according to Formula 1

R-B-A-B-R  (1)

wherein A is a hydrophilic polymer, B a hydrophobic polymer and R are end-groups, wherein R is a C1-C30 organic moiety, wherein A is polyethyleneglycol (PEG) having a molecular weight between 180 and 700 g/mol, wherein a number average molecular weight (Mn) of the triblock copolymer is within the range of 700-2500 g/moL, and wherein the copolymer is fluid in a temperature range of 0° C. to 37° C.

2. The copolymer according to claim 1, wherein the copolymer has a viscosity determined at 20° C. having a value below 30 Pa·s, as determined by shear rheology.

3. The copolymer according to claim 1, wherein the copolymer has a Tg (midpoint) below −20° C.

4. The copolymer according to claim 1, wherein the copolymer has a Tm (midpoint) below 20° C.

5. The copolymer according to claim 1, wherein each B block is a combination of ε-caprolactone with anyone of lactide, glycolide, δ-valerolactone, p-dioxanone or trimethylenecarbonate; or a combination of δ-valerolactone with anyone of lactide, glycolide, p-dioxanone or trimethylenecarbonate; or a combination of p-dioxanone with lactide, glycolide or trimethylenecarbonate; or a combination of trimethylenecarbonate with lactide or glycolide.

6. The copolymer according to claim 1, wherein R is chosen from fatty acid residues, ether residue or urethane residue.

7. The copolymer according to claim 1, wherein R is chosen from an acetyl group, a propionyl group, a hexanoyl group, a nonanoyl group, a dodecanoyl group, pentadecanoyl group, a stearoyl group or a benzoyl group, and wherein R is linear, branched or cyclic and R can be optionally substituted with heteroatoms.

8. The copolymer according to claim 1, wherein the copolymer has a viscosity determined at 20° C. having a value below 20 Pa·s as determined by shear rheology, wherein the copolymer has a Tg (midpoint) below −30° C., wherein the copolymer has a Tm (midpoint) below 10° C., and wherein the copolymer has a number average molecular weight (Mn) between 600 and 3,000 g/mol.

9. The copolymer according to claim 8, wherein the copolymer has a viscosity determined at 20° C. having a value below 10 Pa·s as determined by shear rheology, wherein the copolymer has a Tg (midpoint) below −40° C., wherein the copolymer has a Tm (midpoint) below 0° C., and wherein the copolymer has a number average molecular weight (Mn) between 700 and 2500 g/mol.

10. The copolymer according to claim 9, wherein each B block is a combination of ε-caprolactone with anyone of lactide, glycolide, δ-valerolactone, p-dioxanone or trimethylenecarbonate; or a combination of δ-valerolactone with anyone of lactide, glycolide, p-dioxanone or trimethylenecarbonate; or a combination of p-dioxanone with lactide, glycolide or trimethylenecarbonate; or a combination of trimethylenecarbonate with lactide or glycolide, and wherein R is chosen from fatty acid residues, ether residue or urethane residue.

11. A process for preparing a pharmaceutical composition, comprising the steps of providing the triblock copolymer according to claim 1, providing at least one therapeutically active agent and mixing the copolymer with the therapeutically active agent.

12. A pharmaceutical composition comprising one or more triblock copolymers according to claim 1, and at least one therapeutically active agent.

13. The pharmaceutical composition according to claim 12, wherein the composition comprises at least 50 wt % of the triblock copolymers, relative to the total weight of the pharmaceutical composition.

14. The pharmaceutical composition according to claim 12, wherein the composition has a dynamic viscosity below or equal to 30 Pa·s at 20° C., as determined by shear rheology.

15. The pharmaceutical composition according to claim 14, wherein the composition has a dynamic viscosity below 20 Pa·s as determined by shear rheology.

16. The pharmaceutical composition according to claim 14, wherein the composition has a dynamic viscosity below 5 Pa·s as determined by shear rheology.

17. A pharmaceutical composition comprising one or more triblock copolymers according to claim 9, and at least one therapeutically active agent.

* * * * *